US012766791B2

(12) United States Patent
Beyer et al.

(10) Patent No.: US 12,766,791 B2
(45) Date of Patent: Oct. 20, 2026

(54) RADIAL PUMP ASSEMBLY AND METHODS OF USING SAME

(71) Applicant: ASPECT BIOSYSTEMS LTD., Vancouver (CA)

(72) Inventors: Simon Beyer, Richmond (CA); Sebastian Steiner, Vancouver (CA); Florentin Wilfart, Victoria (CA); Shaun Laidlow, Vancouver (CA); Keddie Brown, Vancouver (CA); Zhensong Xu, Vancouver (CA); Henrik Persson, Vancouver (CA); Navid Hakimi, Vancouver (CA); Adam Looker, Gananoque (CA)

(73) Assignee: ASPECT BIOSYSTEMS LTD., Vancouver (CA)

( * ) Notice: Subject to any disclaimer, the term of this patent is extended or adjusted under 35 U.S.C. 154(b) by 0 days.

(21) Appl. No.: 18/720,546

(22) PCT Filed: Dec. 16, 2022

(86) PCT No.: PCT/CA2022/051855
§ 371 (c)(1),
(2) Date: Jun. 14, 2024

(87) PCT Pub. No.: WO2023/108302
PCT Pub. Date: Jun. 22, 2023

(65) Prior Publication Data

US 2025/0058522 A1 Feb. 20, 2025

Related U.S. Application Data

(60) Provisional application No. 63/290,595, filed on Dec. 16, 2021.

(51) Int. Cl.
*B29C 64/336* (2017.01)
*B01L 3/00* (2006.01)
(Continued)

(52) U.S. Cl.
CPC ...... *B29C 64/336* (2017.08); *B01L 3/502715* (2013.01); *B29C 64/118* (2017.08);
(Continued)

(58) Field of Classification Search
None
See application file for complete search history.

(56) References Cited

U.S. PATENT DOCUMENTS

| | | | | |
|---|---|---|---|---|
| 2,754,835 A * | 7/1956 | Casady | A61M 5/001 | 134/186 |
| 3,447,479 A * | 6/1969 | Rosenberg | F04B 9/02 | 604/152 |

(Continued)

FOREIGN PATENT DOCUMENTS

| | | | |
|---|---|---|---|
| GB | 1232655 A | 5/1971 | |
| WO | WO 2014197999 A1 | 12/2014 | |
| WO | WO 2015107333 A1 | 7/2015 | |
| WO | WO-2017221669 A1 * | 12/2017 | G01N 35/00 |

OTHER PUBLICATIONS

Heinrich, MA et al., "3D Bioprinting: from Benches to Translational Applications", Small, vol. 15(23): 1805510 (2019).

*Primary Examiner* — Yung-Sheng M Tsui
(74) *Attorney, Agent, or Firm* — Todd Lorenz

(57) ABSTRACT

Aspects of the disclosure include a pump assembly comprising a plurality of pumps (e.g. syringe pumps) positioned in a radial array on a mounting bracket. In embodiments, each syringe pump of the plurality of syringe pumps comprises a housing comprising a syringe retainer and a plunger driver. The pump assembly serves to minimize internal volume when used as part of a multi-channel microfluidic bioprinting system.

27 Claims, 24 Drawing Sheets

(51) Int. Cl.

| | |
|---|---|
| ***B29C 64/118*** | (2017.01) |
| ***B29C 64/209*** | (2017.01) |
| ***B29C 64/393*** | (2017.01) |
| ***B33Y 30/00*** | (2015.01) |
| ***B33Y 40/00*** | (2020.01) |
| ***B33Y 50/02*** | (2015.01) |
| ***F04B 23/06*** | (2006.01) |
| *C12N 5/00* | (2006.01) |

(52) U.S. Cl.

CPC .......... *B29C 64/209* (2017.08); *B29C 64/393* (2017.08); *B33Y 30/00* (2014.12); *B33Y 40/00* (2014.12); *B33Y 50/02* (2014.12); *F04B 23/06* (2013.01); *B01L 2200/0647* (2013.01); *C12N 5/0062* (2013.01)

(56) References Cited

U.S. PATENT DOCUMENTS

| | | | | |
|---|---|---|---|---|
| 11,478,586 | B2 * | 10/2022 | Joseph | A61M 5/31575 |
| 2004/0154690 | A1 * | 8/2004 | Osborne | B65B 7/2821 141/27 |
| 2011/0184383 | A1 * | 7/2011 | Hasegawa | A61M 5/1456 604/151 |
| 2014/0183792 | A1 * | 7/2014 | Leu | B33Y 10/00 264/401 |
| 2015/0093465 | A1 | 4/2015 | Page et al. | |
| 2015/0140147 | A1 * | 5/2015 | Konstantinos | B29C 64/241 425/174 |
| 2017/0021566 | A1 | 1/2017 | Lund | |

* cited by examiner

RADIAL PUMP ASSEMBLY AND METHODS OF USING SAME

CROSS-REFERENCE TO RELATED APPLICATION

This application claims priority from U.S. provisional patent application No. 63/290,595 filed on Dec. 16, 2021. The contents of this earlier filed application are hereby incorporated by reference in their entirety.

FIELD OF DISCLOSURE

The present disclosure relates generally to three-dimensional (3D) printing and the generation of three-dimensional biological structures from digital files. Specifically, the invention relates to a multi-channel microfluidic bioprinting system including a radial pump assembly comprising, for example, one or more syringe pumps.

BACKGROUND OF THE DISCLOSURE 3D printing, a form of additive manufacturing (AM), is a process for creating three-dimensional objects directly from digital files. Software is used to slice a computer aided design (CAD) model or a 3D scan of an object into a multitude of thin cross-sectional layers. This collection of layers is sent to the AM system where the system builds the three-dimensional object layer by layer. Each layer is deposited on top of the previous layer until the object has been fully constructed. Various AM processes exist that can build parts in plastic, metal, ceramic and/or biological materials. For example, 3D bioprinting is a particular form of additive manufacturing, defined as the spatial patterning of living cells, biological materials, or their combination in a precisely controlled fashion (Heinrich, M A et al. *Small* 15:1805510 (2019)).

Notably, 3D bioprinting often requires the precise and accurate delivery of rare and/or limited materials in the form of bioinks, e.g. cell samples and the like. Microfluidic 3D bioprinting in particular also requires simultaneous delivery of bioinks to form complex multishelled fibers and 3D constructs. While conventional syringe pumps are well suited to deliver precise and accurate flow rates, when used in parallel formation the rectangular cross section of currently available designs creates a large footprint and inconsistent flow paths between syringes. As the number of syringe pumps used in conjunction with any microfluidic print head is increased, the distance between syringe tips and the print head necessarily increases as well, and this distance will be inconsistent between different pumps. The increased distance requires increased tubing length to couple syringe tips to the print head, which in turn results in an increase in internal volume associated with the tube length. Hence, the greater the number of syringe pumps used for a particular microfluidic device, the greater the amount of internal volume in the system. Internal volume is particularly undesirable in cases where living cells and/or other biological material are used, as they can be challenging to obtain in high numbers and/or substantial volume. Furthermore, the reliance on tubing between syringe tips and the print head introduces challenges with regard to attaching the tubing in an aseptic manner, which is an important consideration when working with living cells. Accordingly, reducing the distance between syringe tip and microfluidic print head, and thus reducing the amount of internal volume in microfluidic systems that rely on multiple syringe pumps would be advantageous and highly desirable.

SUMMARY OF DISCLOSURE

The present invention addresses and resolves the foregoing problems in the art with a radial pump assembly configured to minimize internal volume in a multi-channel microfluidic bioprinting system, comprising a plurality of pumps positioned in a radial array on a mounting bracket, wherein each pump of the plurality of pumps comprises a housing and a retainer for securing the pump. In embodiments, the plurality of pumps are positioned between 10 and 170 degrees relative to each other. In embodiments, one or more of the plurality of pumps are removably attached to respective syringe bays on the mounting bracket. In embodiments, the housing may be wedge-shaped. In exemplary embodiments, the housing of each pump magnetically attaches to a respective syringe bay on the mounting bracket.

In embodiments, the plurality of pumps comprises at least two, three, four, five, six, seven, eight, nine, ten, eleven, or twelve pumps. In embodiments, one or more of the plurality of pumps is a syringe pump, and preferably more than one, most (e.g. all but one or two), or all of the plurality of pumps are syringe pumps. In embodiments, the plurality of pumps further comprises at least one peristaltic pump, constant-flow dual piston pump, gear pump, or combinations thereof.

In one aspect, a pump assembly is provided comprising a plurality of syringe pumps positioned in a radial array on a mounting bracket, wherein each syringe pump of the plurality of syringe pumps comprises a housing comprising a syringe retainer and a plunger driver. In embodiments, the plurality of syringe pumps are positioned in a radial array between 10 and 170 degrees relative to each other. In embodiments, one or more of the plurality of syringe pumps are removably attached to respective syringe bays on the mounting bracket. In embodiments, the housing of each syringe pump magnetically attaches to a respective syringe bay on the mounting bracket.

In embodiments, the syringe pump assembly further comprises at least one syringe having a syringe barrel retained in place by the syringe retainer in one of said syringe pumps. In embodiments, the syringe further comprises a syringe plunger slidably engaged with the syringe barrel and a plunger flange received by a plunger cap adjacent the plunger driver. In embodiments, the plunger cap is configured to receive plunger flanges of differing dimensions. In embodiments, the plunger cap comprises a concave surface for receiving the plunger driver. In exemplary embodiments, the concave surface comprises an inverted cone.

In embodiments, the syringe pump comprising the syringe further comprises one of a plurality of removable plunger clips for securing the plunger flange within the plunger cap, each of said plunger clips comprising a recess of different dimensions for fittingly engaging different syringe plunger diameters. In exemplary embodiments, the plunger clip magnetically attaches to the plunger driver.

In embodiments, the syringe retainer comprises one of a plurality of removable syringe barrel supports, each of said syringe barrel supports comprising a recess of different dimensions for fittingly engaging different syringe barrel diameters. In embodiments, each of the syringe barrel supports further comprises a slot configured to receive and secure a syringe barrel flange.

In embodiments of the syringe pump assembly, a syringe barrel centerline is maintained constant between syringes of different dimensions.

In some embodiments, the at least one syringe is a disposable syringe, optionally wherein the disposable syringe differs in size between 0.2 mL and 50 mL.

In another aspect, a multi-channel microfluidic bioprinting system is provided comprising a print head comprising a plurality of fluid inlets and a plurality of microfluidic printing channels corresponding to each fluid inlet, wherein the plurality of microfluidic channels merge into a single dispensing channel leading to a dispensing orifice; a pump assembly, for example the pump assembly described above; an adaptor comprising a plurality of syringe inlets and corresponding microfluidic adaptor channels for fluidly connecting one or more syringe pumps to said print head; a receiving surface for receiving a first layer of materials dispensed from the orifice; a positioning unit for positioning the receiving surface in three dimensional space with respect to the dispensing orifice, the positioning unit operably coupled to the receiving surface; and a programmable control processor for controlling the positioning unit and for controlling each syringe pump.

In some embodiments, the syringe pump assembly comprises a plurality of syringes retained in a plurality of the syringe pumps. In embodiments, the tips of the syringes insert directly into corresponding fluid inlets in the adaptor. In embodiments, the syringe tips further comprise an elbow connector for inserting into corresponding fluid inlets in the adaptor. In embodiments, a tip of a central syringe inserts directly into a fluid inlet of the print head, thereby bypassing the adaptor.

In embodiments, the microfluidic adaptor channels and/or the microfluidic printing channels further comprise valves, optionally wherein the valves are one-way check valves.

In embodiments, the multi-channel microfluidic bioprinting system further comprises a fluid removal component that is configured to remove an excess fluid that is dispensed from the print head.

In embodiments, the multi-channel microfluidic bioprinting system further comprises a camera configured to capture a machine-readable image included as part of the print head. In embodiments, the machine-readable image is a quick response (QR) code. In embodiments, the programmable control processor provides a visual alert to a user of the system upon acquisition of the machine-readable image, the visual alert comprising an indication to the user of where to attach one or more of the syringe pumps to the mounting bracket, and/or in which syringe pumps to insert a syringe. In embodiments, the visual alert is based on one or more lights on the mounting bracket and/or syringe pumps.

In embodiments, the multi-channel microfluidic bioprinting system further comprises a ring-shaped light module configured to surround a transparent dispensing channel proximal to the orifice and/or the bioprinted fiber as it is dispensed from the orifice.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Figure 1A:
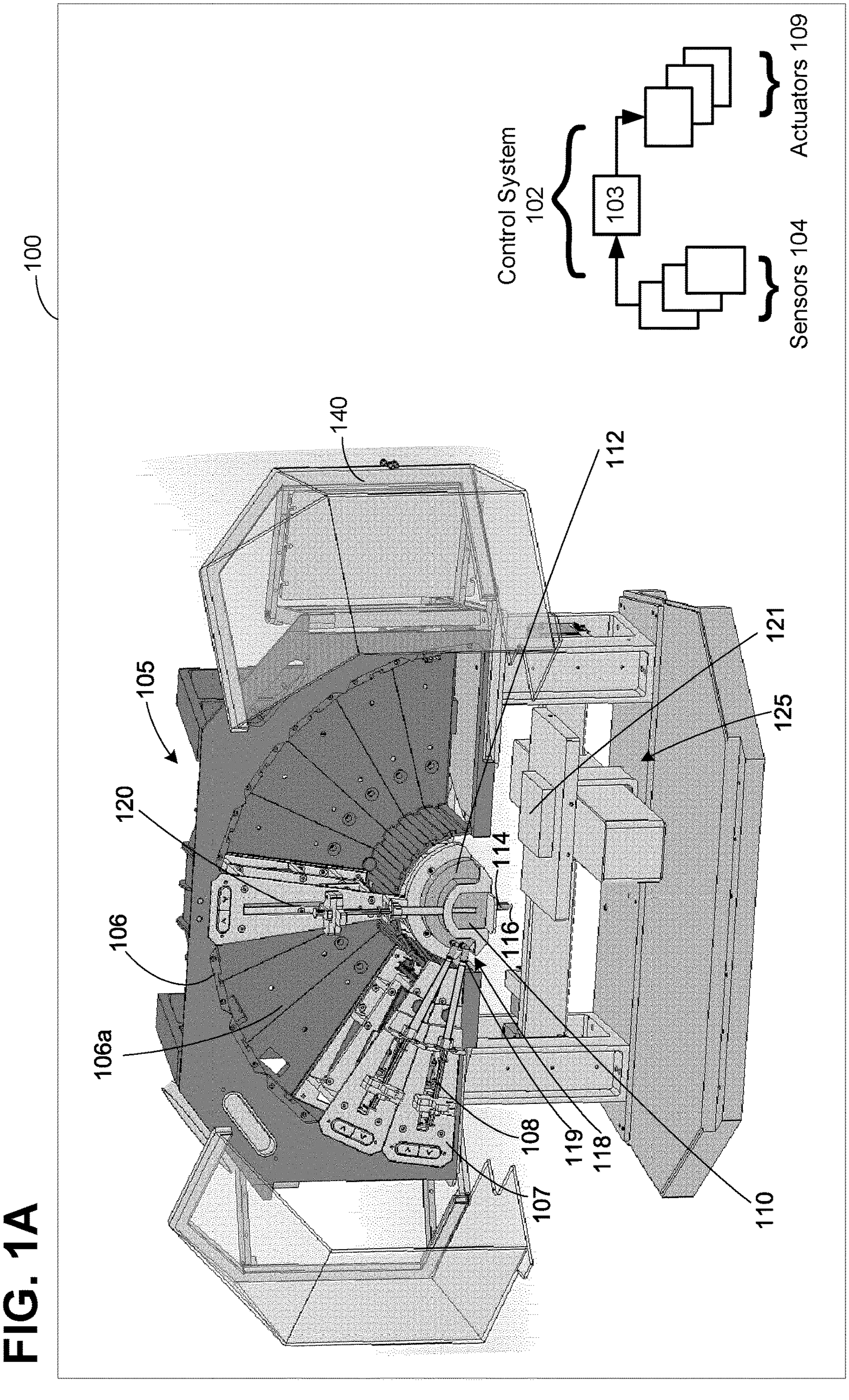
FIG. 1A is an illustration of a microfluidic printing system of the present disclosure with a plurality of syringe pumps attached to a mounting bracket, the microfluidic printing system including an enclosure system illustrated in an open configuration.

The radial pump assembly of the present disclosure advantageously reduces flow path length between, for example, tips of syringes associated with syringe pumps and corresponding inputs into an adaptor and/or print head of the present disclosure, as compared to other systems that do not rely on the disclosed radial pump assembly. For example, systems designed in a manner in which pumps are arranged in parallel (or other non-radial configuration) have substantially longer and heterogeneous flow path lengths as compared to the radial pump assembly of the present disclosure, for a same number of pumps. Moreover, the radial pump assembly of the present disclosure also reduces variability in flow path lengths, for example between different syringe pumps in conventional longitudinal arrays and the corresponding inputs into an adaptor and/or print head. Hence, the radial pump assembly of the present disclosure enables both shorter and more uniform flow path lengths, which correspondingly reduces the amounts of materials needed to produce bioprinted fibers. This is particularly advantageous for materials which are challenging and/or costly to obtain (e.g., biological materials), and can also improve sterility, by reducing or avoiding altogether the need to rely on tubing to fluidically couple syringe tips to the adaptor and/or print head.

Definitions

For purposes of interpreting this specification, the following definitions will apply, and whenever appropriate, terms used in the singular will also include the plural and vice versa. In the event that any definition set forth conflicts with any document incorporated herein by reference, the definition set forth below shall control. Unless defined otherwise, all technical and scientific terms used herein have the same meaning as commonly understood by one of ordinary skill in the art to which the disclosure pertains.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, "w/v" refers to the weight of the component in a given volume of solution.

"Ranges": throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The term "internal volume" as used herein refers to the volume of material that resides within the channels of a microfluidic device. The internal volume is the sum of the swept and the dead volumes. Microfluidic swept volume is the portion of the internal volume that is directly within the material flow path and microfluidic dead volume is the portion of the internal volume that is not directly within the flow path. It is generally best to have the internal volume as low as possible. As used herein, the internal volume is calculated from the tip of the syringe to the start of the dispensing channel of the microfluidic print head.

Printing Systems:

Aspects of the invention include printing systems and associated components that are configured to work with print heads as herein discussed, to carry out the subject methods. Turning to FIG. 1A, depicted is an example illustration of a printing system 100 of the present disclosure. Aspects of printing system 100 may be controlled at least partially by a control system 102, including controller 103. Control system 102 is shown receiving information from a plurality of sensors 104 (various examples of which are described herein) and sending control signals to a plurality of actuators 109 (various examples of which are described herein). As examples, sensors 104 may include pressure sensors, flow sensors, temperature sensors, one or more cameras (e.g., 2, 3, 4, 5), and the like. Actuators 109 may comprise linear actuators, rotary actuators, hydraulic actuators, pneumatic actuators, electric actuators, thermal actuators, magnetic actuators, mechanical actuators, and the like.

Printing system 100 comprises a radial syringe pump assembly 105. Radial syringe pump assembly 105 includes a mounting bracket 106. Mounting bracket 106 may be configured to receive a plurality of syringe pumps 107 for attachment thereto. In embodiments, the plurality of syringe pumps 107 are positioned in corresponding syringe bays 106*a* on mounting bracket 106 in a semi-circular arc, and the syringe pumps 107 may be comprised of a housing. In embodiments, radial syringe pump assembly 105 may be configured to receive at least 3 syringe pumps 107. In embodiments, radial syringe pump assembly 105 may be configured to receive an odd number of syringe pumps 107, for example 3, 5, 7, 9, or 11 syringe pumps 107, In embodiments, radial syringe pump assembly 105 may be configured to receive an even number of syringe pumps 107, for example 2, 4, 6, 8, or 10 syringe pumps 107. Each of syringe pumps 107 may be configured to hold a syringe 108, comprised of a syringe barrel and a plunger. In embodiments, syringe pumps 107 are positioned in a radial array between 10 and 170 degrees relative to each other. In embodiments, syringe pumps 107 are positioned in a radial array between 10 and 170 degrees relative to each other.

Figure 1B:
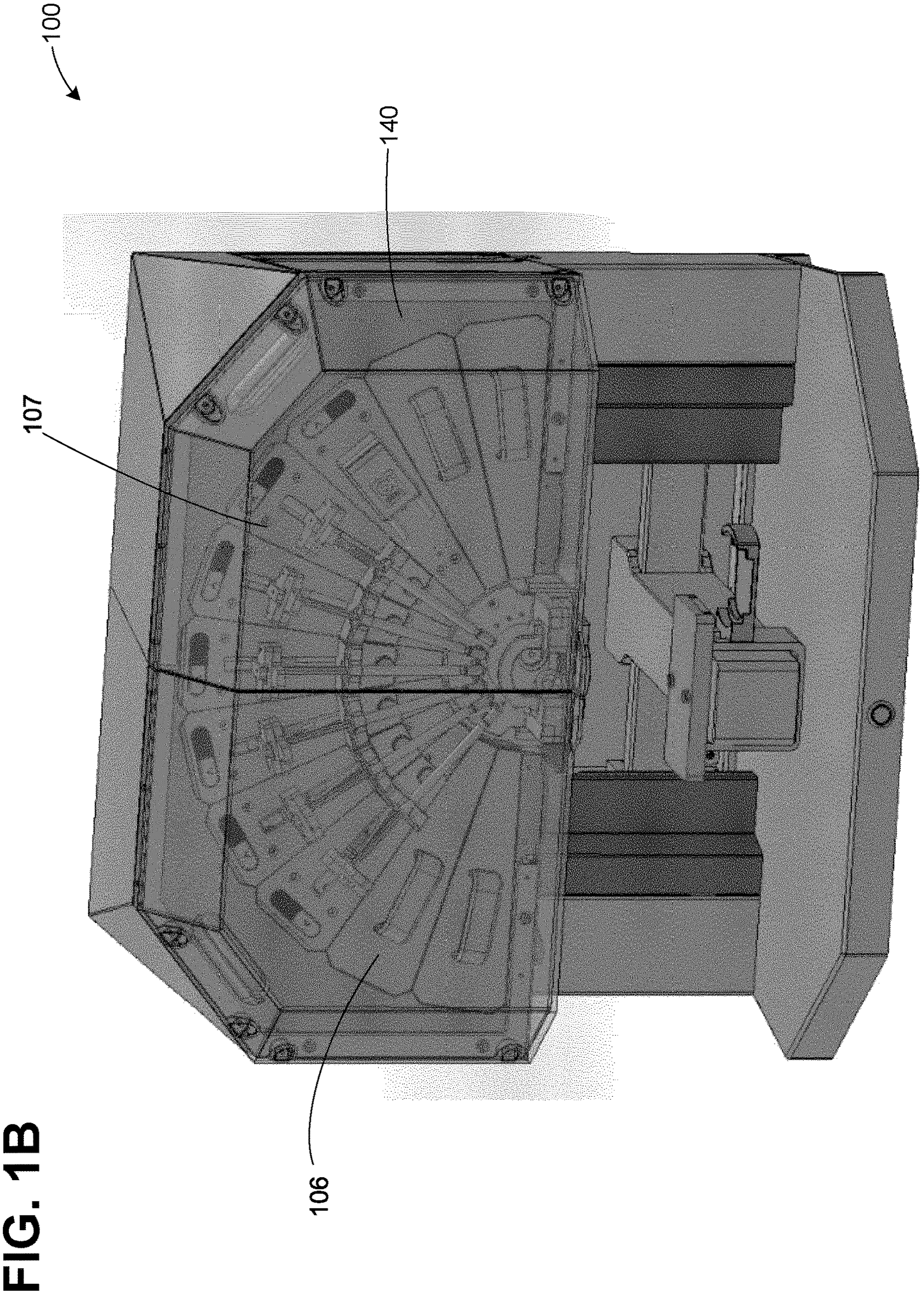
FIG. 1B is an illustration of the microfluidic printing system of FIG. 1A in which the enclosure system is depicted in a closed configuration.

In embodiments, one or more syringe pumps (e.g., syringe pump 107) can be removed and/or added to a printing system (e.g., printing system 100) before and/or after a printing process. Accordingly, in embodiments, the subject syringe pumps are modular components of the subject printing systems, and may be removably attached (i.e., removed, re-attached, or replaced) to the syringe pump assembly 105 via a suitable attachment mechanism of the syringe pump assembly 105. The syringe pump assembly 105 of the printing system 100 is not limited solely to syringe pumps 107 such as shown in FIGS. 1A-2, and different types of pumps (e.g. at least one peristaltic pump, constant-flow dual piston pump, gear pump, or combinations thereof) may be attached to the syringe pump assembly 105 in addition to, or instead of, the one or more syringe pumps.

In embodiments, printing system 100 comprises at least one print head 110, examples of which are described in detail herein. Broadly speaking, print head 110 may comprise a plurality of fluid inlets (not shown at FIG. 1A) and a plurality of microfluidic printing channels (not shown at FIG. 1A) corresponding to each fluid inlet. In embodiments, the plurality of microfluidic printing channels within the print head merge into a single dispensing channel 114 leading to a dispensing orifice 116. In some embodiments, print heads of the present disclosure may include a series of fluid focusing chambers (not shown at FIG. 1A) that consecutively merge the respective microfluidic printing channels into the dispensing channel 114.

In embodiments, printing system 100 further comprises an adaptor 112. In some embodiments, adaptor 112 comprises a plurality of syringe inlets 118, two of which are shown for illustrative purposes at FIG. 1A. Syringe inlets 118 may be fluidly coupled to microfluidic adaptor channels (not shown at FIG. 1A) present within adaptor 112, which in turn may fluidly couple to fluid inlets corresponding to print head 110. In this way, adaptor 112 may fluidly connect one or more of syringe pumps 107, and corresponding syringes 108, to print head 110. In embodiments, syringes 108 can be fluidly coupled to syringe inlets 118 by way of elbow connectors 119 (e.g., connectors having a 90° angle). In other embodiments, syringes 108 can be fluidly coupled to adaptor 112 via connectors having a different angle, for example an angle between 0° and 90°.

In embodiments, one or more print heads (e.g., print head 110) can be removed and/or added to a printing system (e.g., printing system 100) before and/or after a printing process. Accordingly, in embodiments, the subject print heads are modular components of the subject printing systems. In embodiments, one or more adaptors (e.g., adaptor 112) can be removed and/or added to a printing system (e.g., printing system 100) before and/or after a printing process. Accordingly, in embodiments, the subject adaptors are modular components of the subject printing systems. In some embodiments, a print head (e.g., 110) and adaptor (e.g., 112) may be bonded together.

In some embodiments, a single syringe, represented here specifically by numeral 120 may be capable to bypass adaptor 112, for direct insertion into a fluid inlet corresponding to the print head 110.

In some embodiments, printing system 100 comprises a receiving surface 120 upon which a first layer of material dispensed from dispensing orifice 116 of print head 110 is deposited. In some embodiments, receiving surface 121 comprises a solid material. In some embodiments, a receiving surface comprises a porous material. For example, in some embodiments, the porosity of the porous material is sufficient to allow passage of a fluid therethrough. In some embodiments, receiving surface 121 is substantially planar, thereby providing a flat surface upon which a first layer of dispensed material can be deposited. In some embodiments, receiving surface 121 has a topography that corresponds to a three dimensional structure to be printed, thereby facilitating printing of a three dimensional structure having a non-planar first layer.

In some embodiments, receiving surface 121 comprises one or more modular components that are configured to be operably coupled to printing system 100, but which are separable from the printing system. In some embodiments, receiving surface 121 is a disposable receiving surface. In some embodiments, receiving surface 121 is configured for sterilization. In some embodiments, an entire fluid path of printing system 100 is disposable, meaning that all components of the printing system that come into contact with one or more fluids involved with the printing process are disposable, and can be removed from the printing system and exchanged for clean components.

In some embodiments, receiving surface 121 is configured to be operably coupled to one or more different receiving vessels. For example, in some embodiments, receiving surface 121 comprises a circular portion that is sized to be operably coupled to a circular receiving vessel (e.g., a multi-well insert). In some embodiments, receiving surface 121 comprises a square or rectangular portion that is sized to be operably coupled to a square or rectangular receiving vessel (e.g., a multi-well plate (e.g., a 6-well plate)). Receiving surfaces in accordance with embodiments of the invention can have any suitable size or geometry to accommodate a suitable receiving vessel.

In embodiments, the printing system described herein may further include means for suspending a bioprinted fiber structure during printing, patterning, and/or processing. In some embodiments, the suspension of the bioprinted fiber structure may involve a frame coupled to a mounting bracket and/or a receiving surface of the printing system. The frame may include a plurality of posts encircling the frame for securing a continuous length of at least one crosslinkable fiber forming the fiber structure. In this way, a fiber structure may be bioprinted in a manner in which the resultant structure is at least partially suspended during one or more of printing, patterning, and/or post-printing processing. Additional features related to the suspension of the bioprinted structure are described in U.S. Patent Application No. 63/342,118, the disclosure of which is hereby incorporated by reference in its entirety.

In embodiments, printing system 100 may comprise an enclosure system 140. In embodiments, enclosure system is configured to enclose at least mounting bracket 106, and any pumps (e.g., syringe pumps 107) attached thereto, as well as the print head (e.g., print head 110) and adaptor (e.g., adaptor 112). In embodiments, enclosure system 140 may be additionally configured to enclose the receiving surface (e.g., receiving surface 121). In embodiments, enclosure system 140 may be configurable in an open conformation (similar to that depicted at FIG. 1A), and a closed conformation (see FIG. 1B). In embodiments, when enclosure system 140 is in a closed conformation as depicted in FIG. 1B, mounting bracket 106, any pumps (e.g., syringe pumps 107) attached thereto, print head (e.g., print head 110), and adaptor (e.g., adaptor 112) may be wholly enclosed within said enclosure system 140. In some embodiments, the receiving surface (e.g., receiving surface 121) may additionally be wholly enclosed within enclosure system 140.

Reliance on an enclosure system (e.g., enclosure system 140) may enable accurate control over parameters including but not limited to temperature, humidity, $O_2$, and $CO_2$. Accurate control over such parameters can enable increased stability and integrity of 3D bioprinted structures, as well as increased cellular survival during and after a bioprinting process under conditions where the 3D bioprinted structure includes cellular material. In embodiments, variables such as temperature, humidity, $O_2$, and $CO_2$ can be controlled within the enclosure system by way of a feedback control system (e.g., proportional integral derivative (PID) controller), see, e.g., Matamoros M, et al. (2020) Micromachines, 11, 999. In embodiments, such a feedback control system can, e.g., stabilize temperature within the enclosure system to a desired temperature (within some margin of error) and/or stabilize humidity within the enclosure system to a desired humidity (within some margin of error). In some additional or alternative embodiments, such a feedback control system can stabilize $CO_2$ to a desired level (e.g., desired ppm within some margin of error). In some additional or alternative embodiments, such a feedback control system can stabilize $O_2$ to a desired level (e.g., desired ppm within some margin of error).

Thus, in embodiments, printing system 100 may comprise one or more of a temperature modulation component, humidity modulation component, an $O_2$ modulation component, and a $CO_2$ modulation component. In embodiments, the temperature modulation component comprises a heater (e.g., radiant heater, convection heater, conductive heater, fan heater, heat exchanger, or any combination thereof). In embodiments, the temperature modulation component comprises a cooling element (e.g., coolant, chilled liquid, Peltier cooler, radiant cooler, a convection cooler, a conductive cooler, a fan cooler, or any combination thereof). The humidity modulation component can comprise, for example, a chamber (e.g., tank) of water that can be vaporized via a piezoelectrical transducer. Control of $O_2$ may be by way of $O_2$ injection. Control of $CO_2$ may be by way of $CO_2$ injection. In embodiments, the temperature modulation component is capable to adjust and/or maintain the temperature within the enclosure system and/or one or more of print head 110, a printer stage, receiving surface 121, an input material, and/or a fluid (e.g., a sheath solution and/or a buffer solution). In embodiments, the temperature modulation component is configured to adjust a temperature to a set point that ranges from about 0 to about 90° C., such as about 1, 2, 3, 4, 5, 10, 15, 20, 25, 30, 35, 40, 45, 50, 55, 60, 65, 70, 75, 80 or 85° C. In embodiments, the humidity modulation component is configured to adjust humidity to between about 30% and 100%, such as about 35%, 40%, 45%, 50%, 55%, 60%, 65%, 70%, 75%, 80%, 85%, 90%, 95%. In embodiments, the $CO_2$ modulation component is configured to adjust $CO_2$ levels to between about 2% to about 15%, such as about 3%, 4%, 5%, 6%, 7%, 8%, 9%, 10%, 11%, 12%, 13%, 14%.

In some embodiments, receiving surface 121 receives excess fluid (e.g., excess sheath fluid and/or excess buffer solution) that is dispensed from the dispensing orifice 116, and that runs off of one or more layers of material dispensed from the dispensing orifice 116.

In some embodiments, printing system 100 comprises a fluid removal component for removing excess fluid (e.g., excess sheath fluid and/or excess buffer solution) from receiving surface 121 where a fiber structure dispensed from the orifice of the print head is deposited, and optionally from a surface of a dispensed fiber structure. During printing, it is possible that excess fluid will collect or "pool" on the receiving surface 121 or on a surface of dispensed fiber structure. Such pooling can interfere with the deposition process. For example, pooled sheath fluid may cause a dispensed fiber to slip from its intended position in a 3D structure being printed. Therefore, in some embodiments, removal of excess sheath fluid from the receiving surface and optionally from a surface of the dispensed fiber structure by way of a fluidic removal component may improve additive manufacturing of three-dimensional structures.

Excess fluid may be removed from the receiving surface 121 or from a surface of one or more layers of dispensed fibers by drawing the fluid off of those surfaces, by allowing or facilitating evaporation of the fluid from those surfaces or, in embodiments where the receiving surface 121 is porous, excess fluid may be removed by drawing it through the porous surface. In some embodiments, an absorptive material (e.g., a sponge) can be used to draw excess fluid away from receiving surface 121.

In some embodiments, receiving surface 121 comprises a vacuum component (not shown at FIG. 1A) that is configured to apply suction from one or more vacuum sources to the receiving surface 121. In some embodiments, receiving surface 121 comprises one or more vacuum channels that are configured to apply suction to the receiving surface. In some embodiments, receiving surface 121 comprising a vacuum component is configured to aspirate an excess fluid from the receiving surface 121 before, during and/or after a printing process is carried out. In some embodiments where receiving surface 121 is porous, the vacuum component may be configured to apply suction to draw excess fluid through the porous surface.

In some embodiments, a receiving surface comprises one or more tubes that are fluidly coupled to a vacuum source, which can provide suction for removing excess fluid from the receiving surface 121, and optionally from a surface of dispensed fiber structure. In such embodiments, a solid or porous receiving surface can also be used. In some embodiments, a print head (e.g., print head 110) is configured to further comprise one or more vacuum channels, the one or more vacuum channels each having an orifice situated near (i.e., adjacent to) the dispensing orifice. When the print head is in fluid communication with a vacuum, the one or more vacuum channels direct negative pressure to an area of the receiving surface 121 where materials are being dispensed or have been dispensed from the dispensing orifice and/or to a portion of the surface area of the dispensed fiber structure, thereby drawing up excess fluid from the receiving surface 121 and optionally from a surface of the dispensed fiber structure, thereby eliminating pooling of fluid on the receiving surface 121 and/or the dispensed fiber structure.

In embodiments, printing system 100 achieves a particular geometry of a dispensed fiber structure by moving a printer stage or receiving surface 121 relative to a print head (e.g., print head 110). In certain embodiments, at least a portion of printing system 110 is maintained in a sterile environment (e.g., within a biosafety cabinet (BSC)). In some embodiments, printing system 100 is configured to fit entirely within a sterile environment.

In some embodiments, printing system 100 comprises a 3D motorized stage 125, also referred to herein as positioning unit 125, comprising at least three arms for positioning the receiving surface 121 in three dimensional space (i.e., along x, y, and z axes of a Cartesian coordinate system) below a print head (e.g., print head 110).

In some embodiments, the 3D motorized stage arms are driven by corresponding motors, respectively, and controlled by a programmable control processor, such as a computer (e.g., component of control system 102). In a preferred embodiment, receiving surface 121 is moveable along all three primary axes of the Cartesian coordinate system by 3D motorized stage 125, and movement of the stage is defined using computer software. It will be understood that the invention is not limited to only the described positioning system, and that other positioning systems are known in the art. As material is dispensed from a dispensing orifice (e.g., dispensing orifice 116) on a print head (e.g., print head 110), the positioning unit 125 is moved in a pattern controlled by software, thereby creating a first layer of the dispensed material on the receiving surface 121. Additional layers of dispensed material are then stacked on top of one another such that the final 3D geometry of the dispensed layers of material is generally a replica of a 3D geometry design provided by the software. The 3D design may be created using typical 3D CAD (computer aided design) software or generated from digital images, as known in the art. Further, if the software generated geometry contains information on specific materials to be used, it is possible, according to one embodiment of the invention, to assign a specific input material type to different geometrical locations. For example, in some embodiments, a printed 3D structure can comprise two or more different input materials, wherein each input material has different properties (e.g., each input material comprises a different cell type, a different cell concentration, a different extracellular matrix (ECM) composition, etc.).

Aspects of printing system 100 include software programs that are configured to facilitate deposition of the subject input materials in a specific pattern and at specific positions in order to form a specific fiber, planar or 3D structure. In order to fabricate such structures, the subject printing systems deposit the subject input materials at precise locations (in two or three dimensions) on receiving surface 121. In some embodiments, the locations at which a printing system deposits a material are defined by a user input, and are translated into computer code. In some embodiments, a computer code includes a sequence of instructions, executable in the central processing unit (CPU) of a digital processing device (e.g., component of control system 102), written to perform a specified task. In some embodiments, printing parameters including, but not limited to, printed fiber dimensions, syringe pump speed, movement speed of the positioning unit 125, and crosslinking agent intensity or concentration are defined by user inputs and are translated into computer code. In some embodiments, printing parameters are not directly defined by user input, but are derived from other parameters and conditions by the computer code.

Aspects of the present invention include methods for fabricating tissue constructs, tissues, and organs, comprising: a computer module receiving input of a visual representation of a desired tissue construct; a computer module generating a series of commands, wherein the commands are based on the visual representation and are readable by printing system 100; a computer module providing the series of commands to a printing system; and the printing system 100 depositing one or more input materials according to the commands to form a construct with a defined geometry.

In some embodiments, the locations at which a printing system deposits an input material are defined by a user input and are translated into computer code. In some embodiments, the devices, systems, and methods disclosed herein further comprise non-transitory computer readable storage media or storage media encoded with computer readable program code. In some embodiments, a computer readable storage medium is a tangible component of printing system 100 (or a component thereof) or a computer connected to printing system 100 (or a component thereof). In some embodiments, a computer readable storage medium is optionally removable from a digital processing device. In some embodiments, a computer readable storage medium includes, by way of non-limiting example, a CD-ROM, DVD, flash memory device, solid state memory, magnetic disk drive, magnetic tape drive, optical disk drive, cloud computing system and/or service, and the like. In some cases, the program and instructions are permanently, substantially permanently, semi-permanently, or non-transitorily encoded on a storage medium.

In some embodiments, the devices, systems, and methods described herein comprise software, server, and database modules. In some embodiments, a "computer module" is a software component (including a section of code) that interacts with a larger computing system (e.g., control system 102). In some embodiments, a software module (or program module) comes in the form of one or more files and typically handles a specific task within a computing system (e.g., control system 102).

In some embodiments, a module is included in one or more software systems. In some embodiments, a module is integrated with one or more other modules into one or more software systems. A computer module is optionally a standalone section of code or, optionally, code that is not separately identifiable. In some embodiments, the modules are in a single application. In other embodiments, the modules are in a plurality of applications. In some embodiments, the modules are hosted on one machine. In some embodiments, the modules are hosted on a plurality of machines. In some embodiments, the modules are hosted on a plurality of machines in one location. In some embodiments, the modules are hosted a plurality of machines in more than one location. Computer modules in accordance with embodiments of the invention allow an end user to use a computer to perform the one or more aspects of the methods described herein.

In some embodiments, a computer module comprises a graphical user interface (GUI). As used herein, "graphic user interface" means a user environment that uses pictorial as well as textual representations of the input and output of applications and the hierarchical or other data structure in which information is stored. In some embodiments, a computer module comprises a display screen. In further embodiments, a computer module presents, via a display screen, a two-dimensional GUI. In some embodiments, a computer module presents, via a display screen, a three-dimensional GUI such as a virtual reality environment. In some embodiments, the display screen is a touchscreen and presents an interactive GUI.

Aspects of the invention can include one or more fluid reservoirs that are configured to store a fluid and deliver the fluid to the printing system (e.g., the print head) through one or more fluid channels, which provide fluid communication between the printing system and the reservoirs. In some embodiments, a printing system comprises one or more fluid reservoirs that are in fluid communication with a fluid channel. In some embodiments, a fluid reservoir is connected to an input orifice of a fluid channel. In some embodiments, a fluid reservoir is configured to hold a volume of fluid that ranges from about 100 pL up to about 1 L, such as about 1, 5, 10, 15, 20, 25, 30, 35, 40, 45, 50, 55, 60, 65, 70, 75, 80, 85, 90, 95 or 100 mL, or such as about 150, 200, 250, 300, 350, 400, 450, 500, 550, 600, 650, 700, 750, 800, 850, 900 or 950 mL. For example, while the above disclosure is discussed with regard to syringe pumps, in additional or alternative embodiments, other types of pumps can be used, provided they are configured for attachment to a mounting bracket of a printing system of the present disclosure in similar fashion as that discussed above for syringe pumps.

Figure 1C:
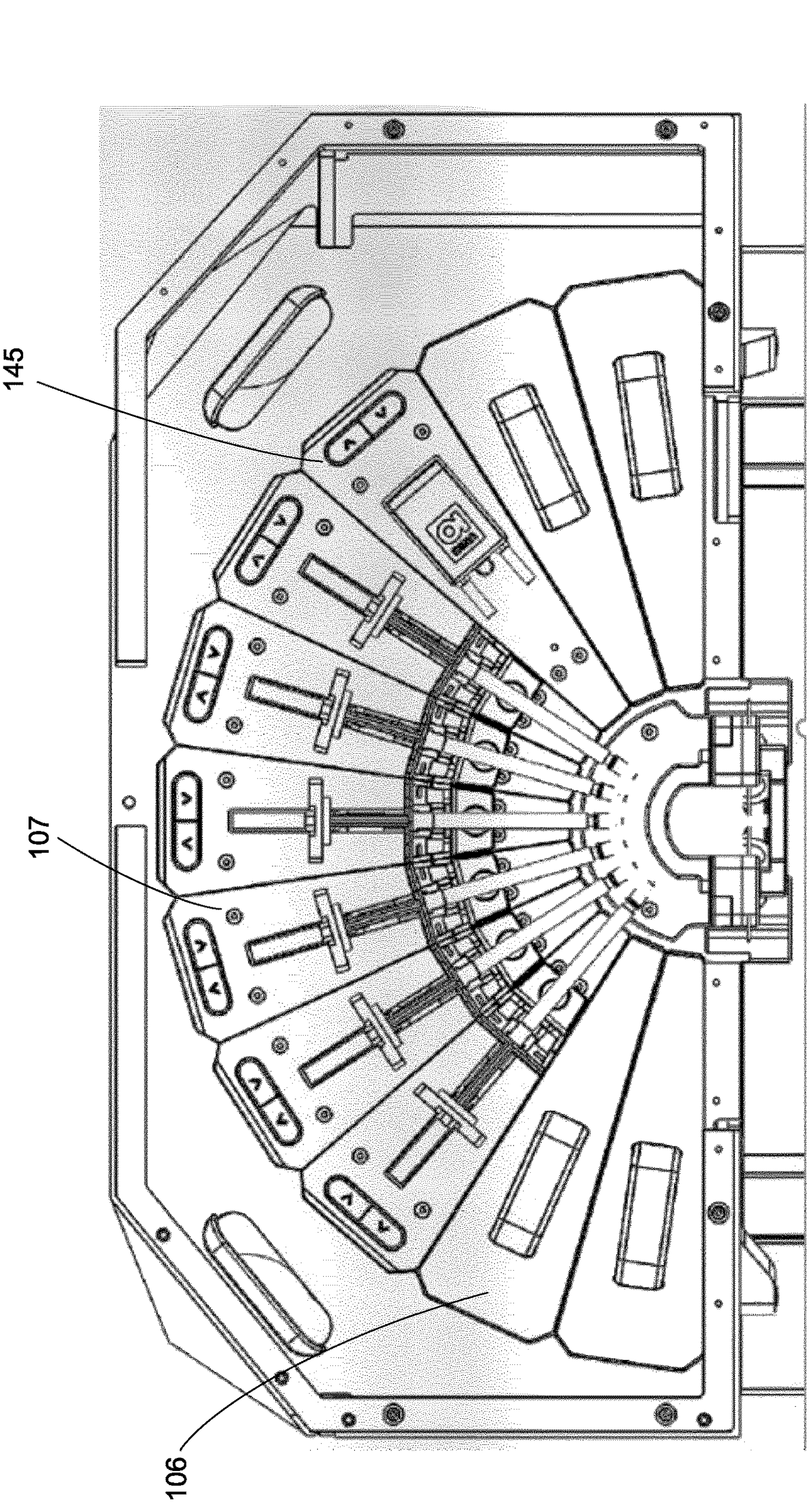
FIG. 1C is another illustration of a portion of the microfluidic printing system of FIGS. 1A-1B, with a plurality of syringe pumps and a single peristaltic pump attached to the mounting bracket.
Figure 2:
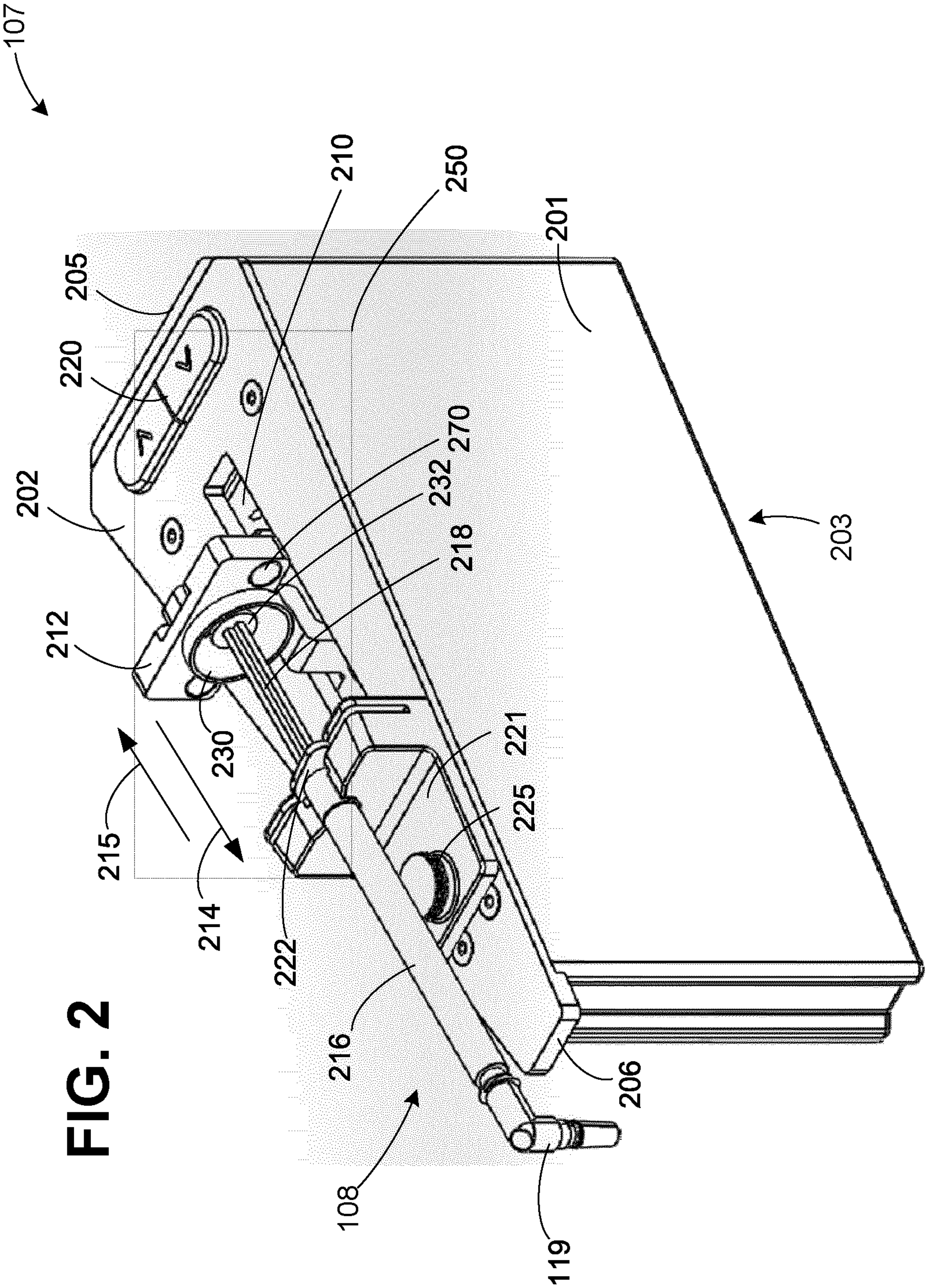
FIG. 2 is an illustration of an embodiment of a syringe pump and associated syringe, capable to be used in conjunction with the microfluidic printing system of FIG. 1A.

Accordingly, in an embodiment, one or more fluid reservoirs can be used in conjunction with at least one peristaltic pump 145 attached to mounting bracket 106, along with a plurality of syringe pumps 107 (see FIG. 1C). In additional or alternative embodiments, one or more fluid reservoirs can be used in conjunction with, e.g., at least one constant-flow dual piston pump, or at least one gear pump. In embodiments, one or more of said fluid reservoirs may be controlled to a desired temperature.

In some embodiments, a printing system comprises a light module for optionally exposing a photo crosslinkable input material to light in order to crosslink the material. Light modules (e.g., ultraviolet (UV) light module) in accordance with embodiments of the invention can be integrated into a print head (e.g., print head 110), or can be a component of printing system 100.

Figure 1D:
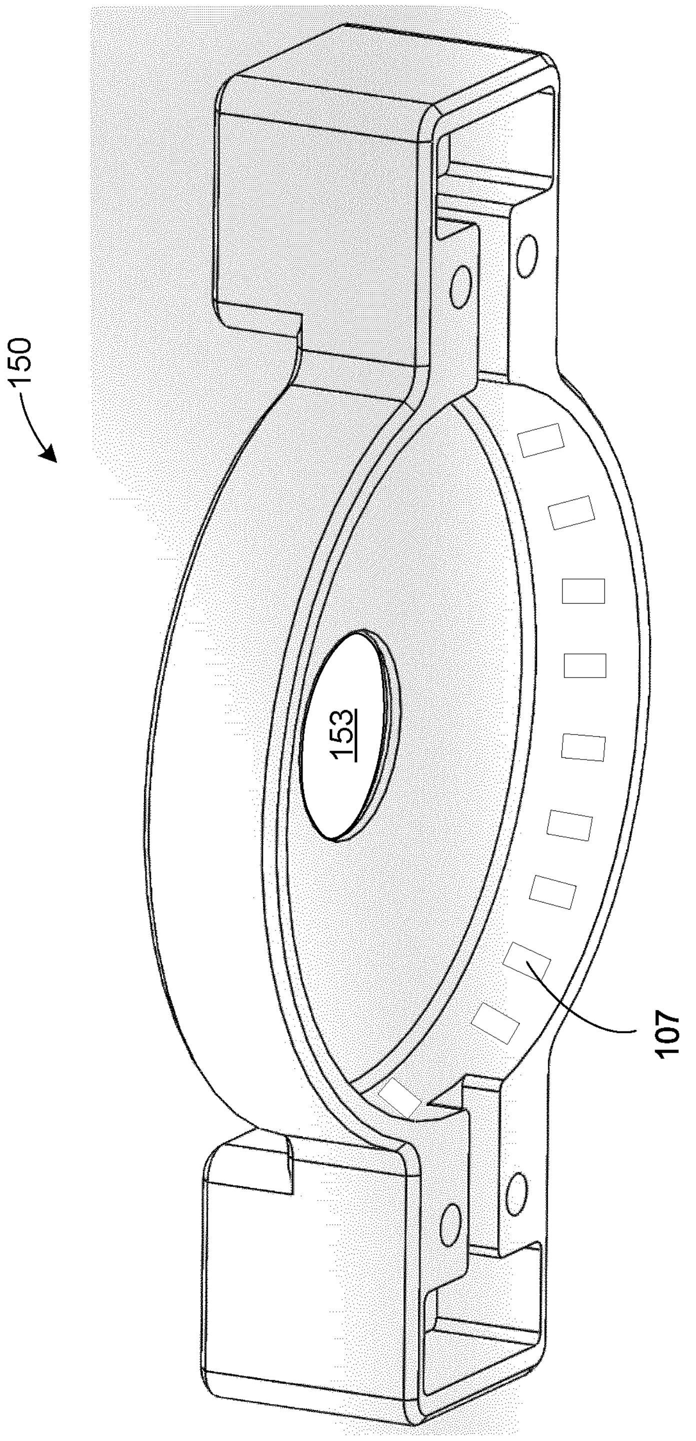
FIG. 1D depicts a ring-shaped light module for use with the microfluidic printing system of FIGS. 1A-1B.

In embodiments, a light module is ring-shaped. Turning to FIG. 1D, depicted is ring-shaped light module 150. In embodiments, ring-shaped light module 150 entirely surrounds a transparent portion of dispensing channel 114 and/or dispensing orifice 116. Specifically, in embodiments, one or more of dispensing channel 114 and/or dispensing orifice 116 extends through central cavity 153. In some embodiments, the ring shaped light module is positioned directly beneath dispensing orifice 116, such that a fiber emanating from dispensing orifice 116 passes through central cavity 153 of ring shaped light module 150 In embodiments, the ring shaped module may surround the dispensing orifice 116, and/or at least a portion of dispensing channel 114.

Figure 1E:
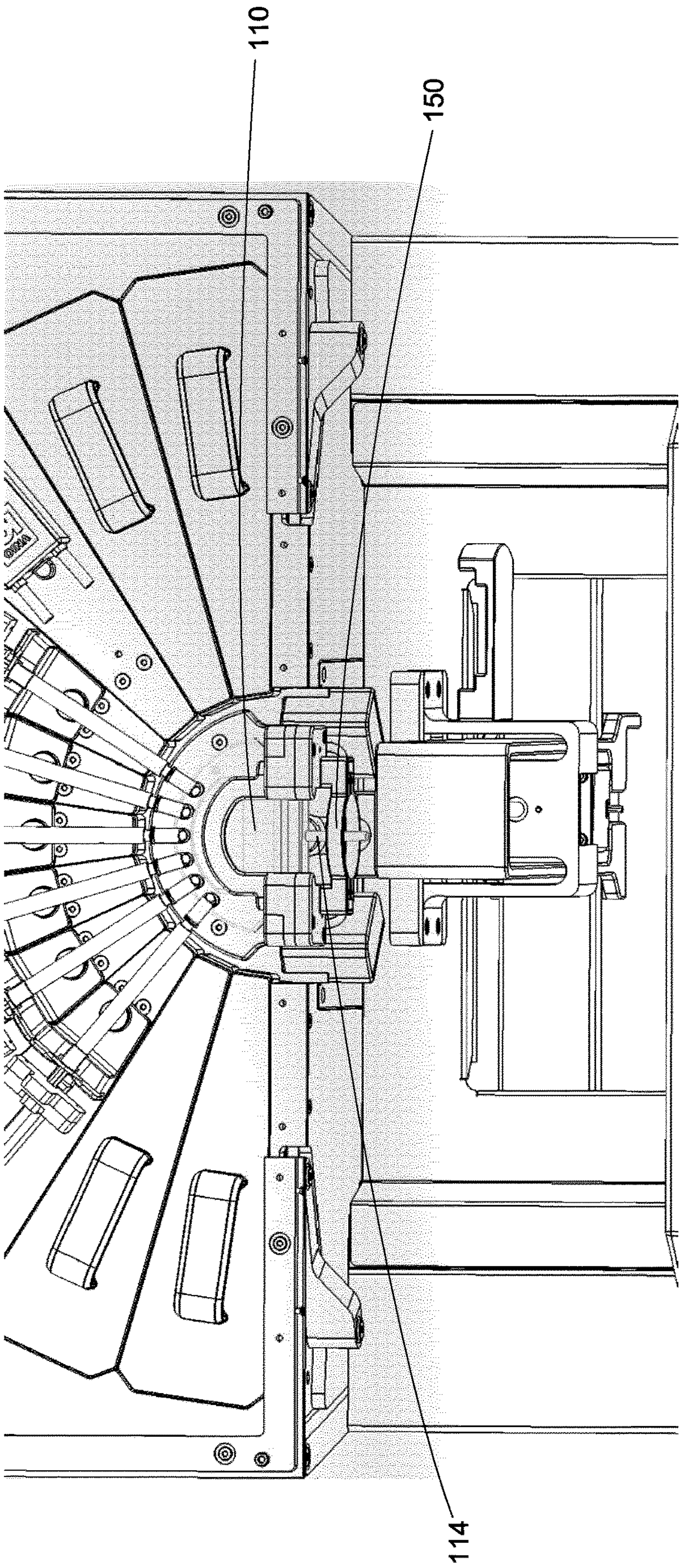
FIG. 1E depicts the ring-shaped light module of FIG. 1D coupled to the microfluidic printing system of FIGS. 1A-1B.

Ring-shaped light module 150 is configured with a plurality of light sources 157 to direct light inward in the direction of a center (i.e., towards central cavity 153) of the ring-shaped light module, such that light is directed circumferentially at a fiber as the fiber is being printed. In embodiments, the plurality of light sources comprises at least between 10 and 40 individual light sources, for example between 15 and 35, for example between 20 and 30. In embodiments, light sources 157 comprise light-emitting diodes (LEDs), for example UV-LEDs. Turning to FIG. 1E, depicted is an illustration of ring-shaped light module 150 coupled to a printing system (e.g., printing system 100), where dispensing channel 114 of print head 110 extends through a central cavity (e.g., central cavity 153) of ring-shaped light module 150.

Figure 1F:
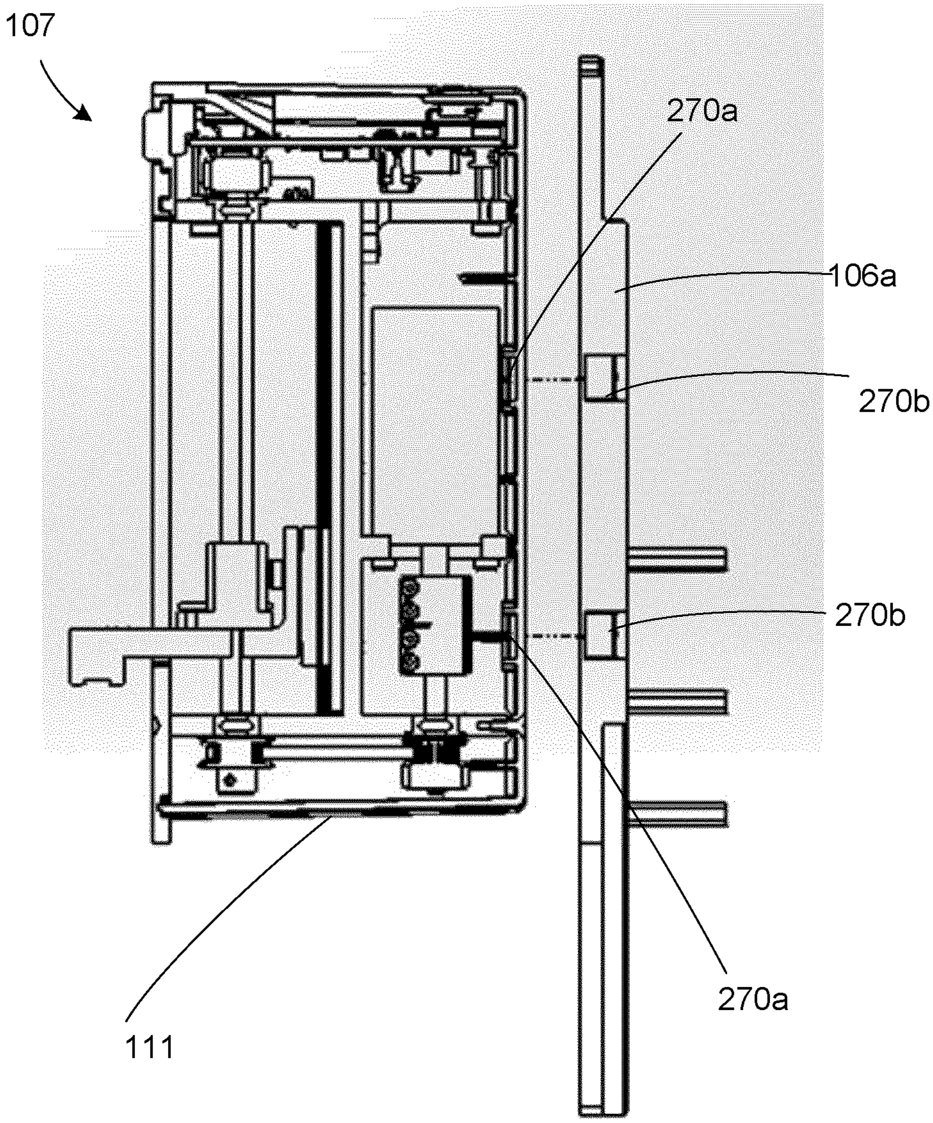
FIG. 1F illustrates a cross-sectional view of the syringe pump 107 secured to a syringe bay in the mounting bracket, according to certain embodiments.

FIG. 1F illustrates a cross-sectional view of the syringe pump 107 secured to a syringe bay backing plate, according to certain embodiments. As illustrated in FIG. 1F, the syringe pump body 107 may have one or more magnets 270*a* at the bottom of the cup 111. According to certain embodiments, the mounting bracket 106 may have one or more magnets 270*b* installed within each individual syringe bay (106*a*) to align the syringe pump 107, and pull and/or maintain it in the correct position/direction in the syringe bay (106*a*).

Figure 1G:
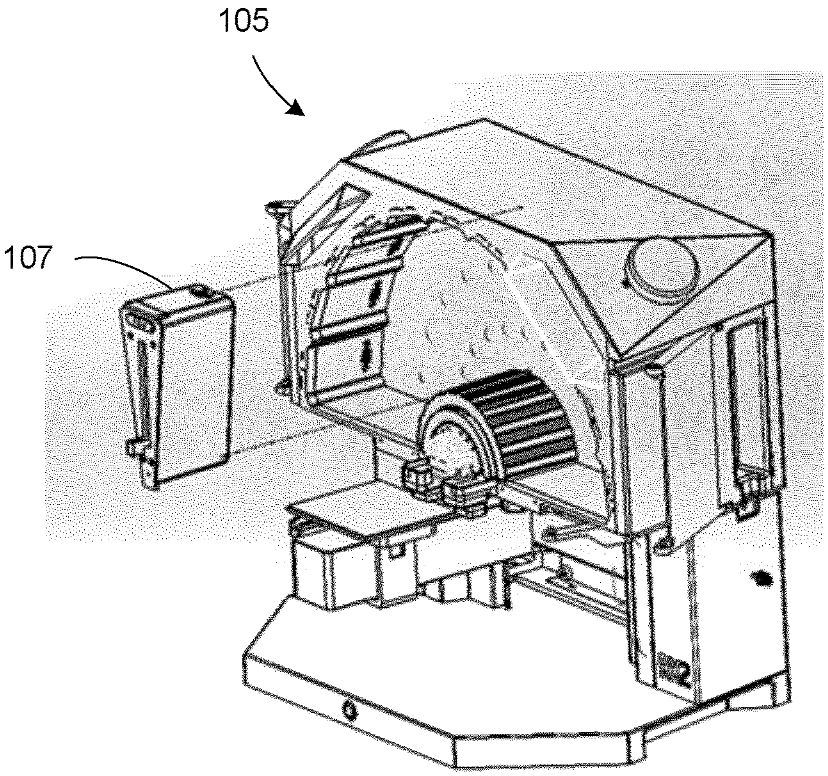
FIG. 1G illustrates an opened syringe pump assembly for receiving the syringe pump, according to certain embodiments.
Figure 1H:
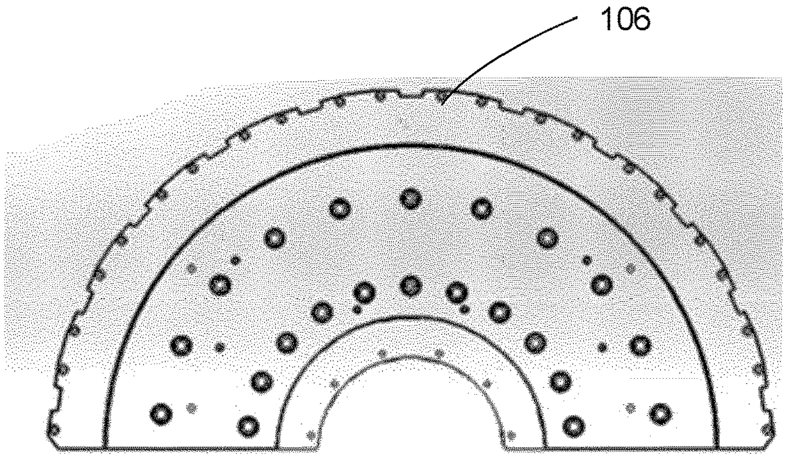
FIG. 1H illustrates the mounting bracket comprising magnetic attachment points for individual syringe bays, according to certain embodiments.

FIG. 1G illustrates an opened syringe pump assembly for receiving the syringe pump, according to certain embodiments, and FIG. 1H illustrates a mounting bracket comprising eleven syringe bays, according to certain embodiments. As illustrated in FIG. 1G, the syringe pump assembly 105 may be configured to receive the syringe pump 107. As described above, the syringe pump body 107 may be magnetically secured to an individual syringe bay (106*a*) in the mounting bracket (106), which may be configured to align the syringe pump 107 to the mounting bracket (106).

Syringe Pumps:

Syringe pumps of the present disclosure comprise those capable to be attached to the printing system illustrated at FIG. 1A (also see FIG. 1B), such that a plurality of syringe pumps can be positioned in a semi-circular arc on mounting bracket 106 of syringe pump assembly 105.

Turning to FIG. 2, depicted is a high-level illustration of an exemplary syringe pump 107. Syringe pump 107 comprises one example of a housing 201 that can be used in conjunction with printing system 100. Syringe pump 107 is comprised of a top 202, and a bottom 203. In the depicted example, each of top 202 and bottom 203 are comprised of a wedge-shape of substantially similar dimensions, although it will be understood that other shapes (e.g., rectangular) are within the scope of this disclosure. As depicted, top 202 comprises a first edge 205 that is of a length longer than that of second edge 206, where top 202 tapers from the longer first edge 205 to the shorter edge 206. Similar logic applies to bottom 203. In this way, a plurality of syringe pumps can be positioned in a radial array on mounting bracket 106 of syringe pump assembly 105.

In embodiments, syringe pump 107 includes a slot 210 in the top 202, from which projects plunger driver 212. As will be elaborated in greater detail below, plunger driver 212 is configured to move in a forward direction, exemplified by arrow 214, and can also move in a reverse direction, exemplified by arrow 215. In this way, plunger driver 212 is capable to drive plunger 218 into barrel 216 of syringe 108 when driven in the forward direction, and is capable to retract plunger 218 from barrel 216 of syringe 108 when driven in the reverse direction (the details of which are elaborated further below). In some embodiments, movement of plunger driver 212 can be controlled by inputs 220 (e.g., push buttons, knobs, and the like). Additionally or alternatively, as discussed above, plunger driver 212 can be controlled via a controller (e.g., controller 103) based on instructions stored, for example, in non-transitory memory. In some embodiments elbow shaped connectors 119 can be used to couple a tip of syringe 108 to the adaptor (e.g., adaptor 112 at FIG. 1A).

Figure 3A:
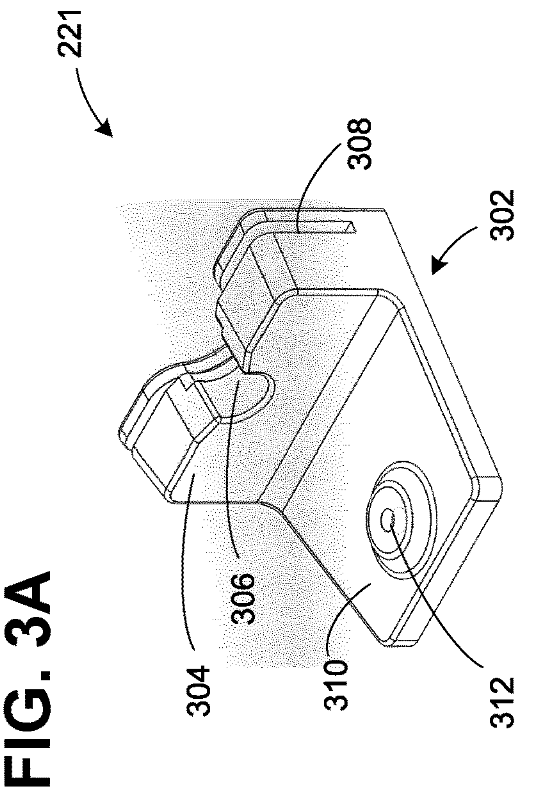
FIGS. 3A-3B depict two different views of an example syringe retainer used in conjunction with the syringe pump illustrated at FIG. 2 for receiving a syringe barrel.
Figure 3B:
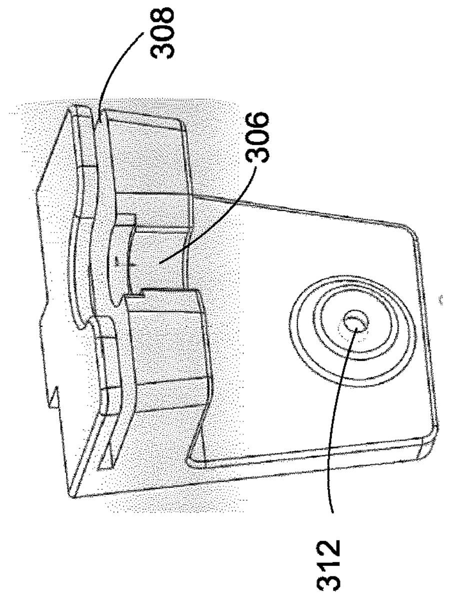

Syringe barrel 216 is held in place via syringe retainer 221. In embodiments, syringe retainer 221 is removable, and can be replaced with a different syringe retainer in order to accommodate syringe barrels of differing sizes. Turning to FIG. 3A, depicted is a close-up view of syringe retainer 221. Syringe retainer 221 is comprised of a flat bottom 302 for placement upon the flat surface of top 202 of syringe pump 107, and further comprises a retainer wall 304 having a recess 306 (e.g., U-shaped recess) configured to fittingly receive a syringe barrel (e.g., syringe barrel 216) of defined dimensions (e.g., defined diameter). In embodiments, syringe retainer 221 further comprises a crevasse 308 in retainer wall 304 configured to fittingly receive a syringe barrel flange, such as syringe barrel flange 222 depicted at FIG. 2. Syringe retainer 221 includes a shelf 310 that extends from retaining wall 304 in the direction of the shorter edge 206 of syringe pump 107. In embodiments, shelf 310 may include female screw component 312, into which a screw 225 (refer to FIG. 2), for example a thumb screw, can be inserted thereto, for securing syringe retainer 221 to top 202 of syringe pump 107. Although the figures depict usage of a thumb screw to secure syringe retainer 221 to syringe pump 107, other attachment means are within the scope of this disclosure, including magnetic, hook and loop (e.g., VELCRO®), adhesive, and the like. FIG. 3B depicts another view of syringe retainer 221.

Figure 3C:
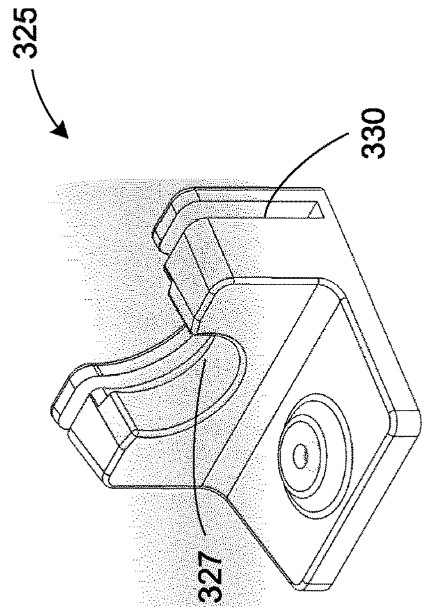
FIG. 3C depicts another example syringe retainer used in conjunction with the syringe pump of FIG. 2, for receiving a syringe barrel of a larger diameter than that depicted at FIGS. 3A-3B.

FIG. 3C depicts another syringe retainer 325. Syringe retainer 325 is substantially similar to syringe retainer 221, except that syringe retainer 325 has a recess 327 (e.g., U-shaped recess) that differs in dimensions from that of syringe retainer 221. Specifically, recess 327 associated with syringe retainer 325 is capable to fittingly receive a syringe barrel of greater dimensions (e.g., greater diameter) than that of 306 associated with syringe retainer 221. Similarly, as diameters change between syringe barrels, so too may the dimensions of an associated barrel flange. Hence, syringe retainer 325 includes crevasse 330, which is of greater overall dimensions than that of crevasse 308, so as to fittingly receive a barrel flange associated with a syringe barrel of a diameter that is fittingly received by recess 327.

Thus, syringe retainer 221 may be capable to securely retain a syringe barrel capable of holding a first volume (e.g., 1 mL), whereas syringe retainer 325 may be capable to securely retain a syringe barrel capable of holding a second volume (e.g., 5 mL). Such examples are illustrative, and it may be understood that any number of syringe retainers similar to those depicted at FIGS. 3A-3B can be used in conjunction with the syringe pumps of the present disclosure. For example, different syringe retainers may correspond to syringes having volumes between 0.1 mL and 20 mL, or even higher than 20 mL, such as 50 mL or even 100 mL. For example and without limitation, individual syringe retainers may be capable to fittingly retain syringes having syringe barrels that hold 0.1 mL, 0.2 mL, 0.3 mL, 0.4 mL, 0.5 mL, 0.6 mL, 0.7 mL, 0.8 mL, 0.9 mL, 1 ml, from 1-2 mL, from 2-3 mL, from 3-4 mL, from 4-5 mL, from 5-6 mL, from 6-7 mL, from 7-8 mL, from 8-9 mL, from 9-10 mL.

Returning to FIG. 2, syringe pump 107 may include a plunger cap 230, positioned adjacent plunger driver 212. In embodiments, plunger cap 230 is concave in the direction of the plunger driver 212, for receipt of a plunger flange 232 associated with plunger 218. In some embodiments, plunger cap 230 may have an overall inward-cone shape for receipt of the plunger flange 232 associated with plunger 218. The concave/inward-cone shape may be such that plunger flanges of different dimensions (e.g., differing length of an outer perimeter, different overall diameter, different thickness, etc.) will adopt somewhat different positions within plunger cap 230. For example, a plunger flange with a greater outer perimeter length may not extend as far into the plunger cap as a plunger flange with a lesser outer perimeter length, due to the plunger flange with the greater outer perimeter length coming into contact with the inner walls of the plunger cap sooner than that of a plunger flange with the lesser outer perimeter length.

While not specifically shown, it is to be understood that there are other ways that the plunger (e.g., plunger 218) can be coupled to the plunger driver (e.g., plunger driver 212), without departing from the scope of this disclosure. For example, the plunger may comprise a threaded portion capable to be received by a corresponding portion of the plunger driver. Such an example is meant to be illustrative and non-limiting. Other attachment methods are within the scope of the present disclosure.

Figure 3D:
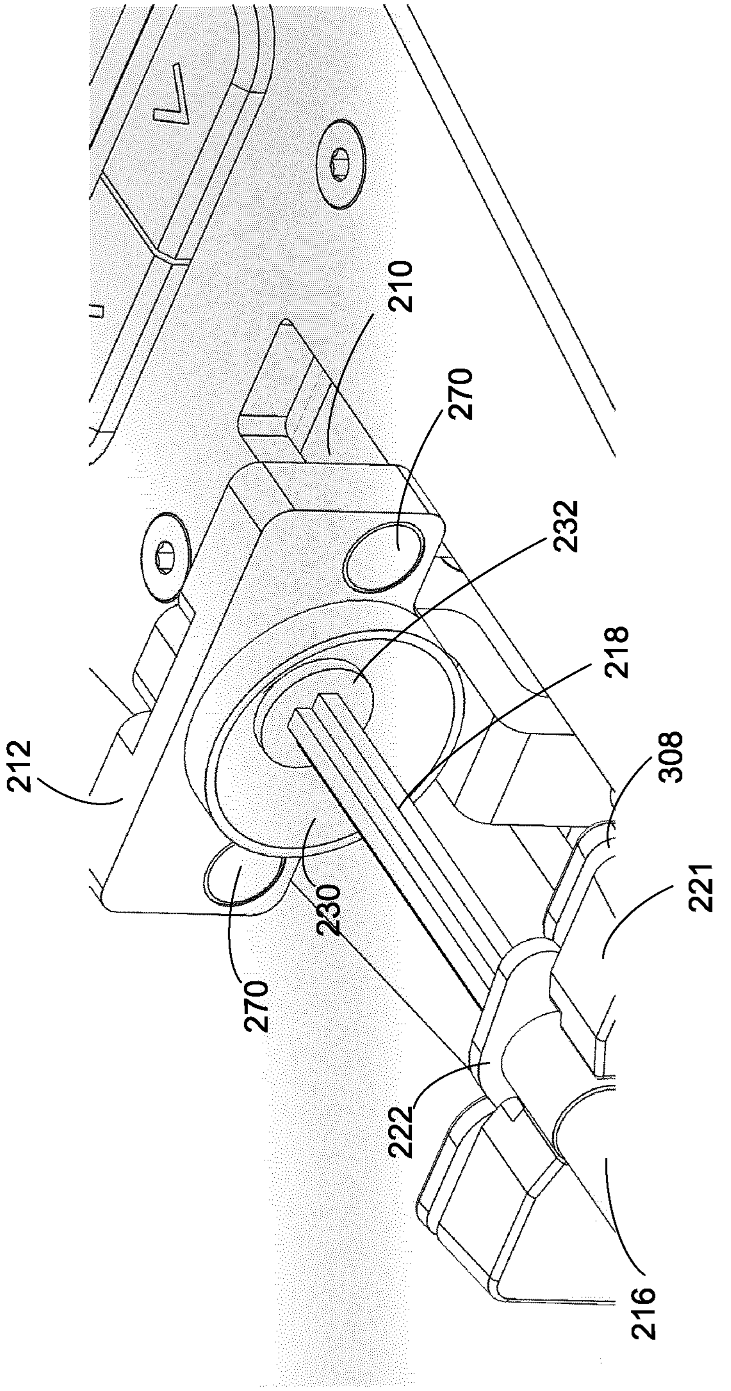
FIG. 3D depicts a close up illustration of a portion of the syringe pump of FIG. 2, showing a portion of a syringe retainer and a plunger driver with corresponding adjacent plunger cap.

A close-up view of the area of syringe pump 107 defined by dashed box 250 is shown at FIG. 3D for reference. As can be seen at FIG. 3D, and which can also be seen at FIG. 2, plunger driver 212 comprises two attachment means 270 for attachment of a plunger clip thereto. In FIG. 2 and FIG. 3D, the plunger clip is not attached, and the attachment elements 270 are thus visible. In embodiments, the attachment means 270 comprise magnets capable to magnetically attract corresponding magnets on the plunger clip, although other attachment elements (screws, buttons, snap fasteners, adhesives, and the like) are within the scope of this disclosure.

Figure 3E:
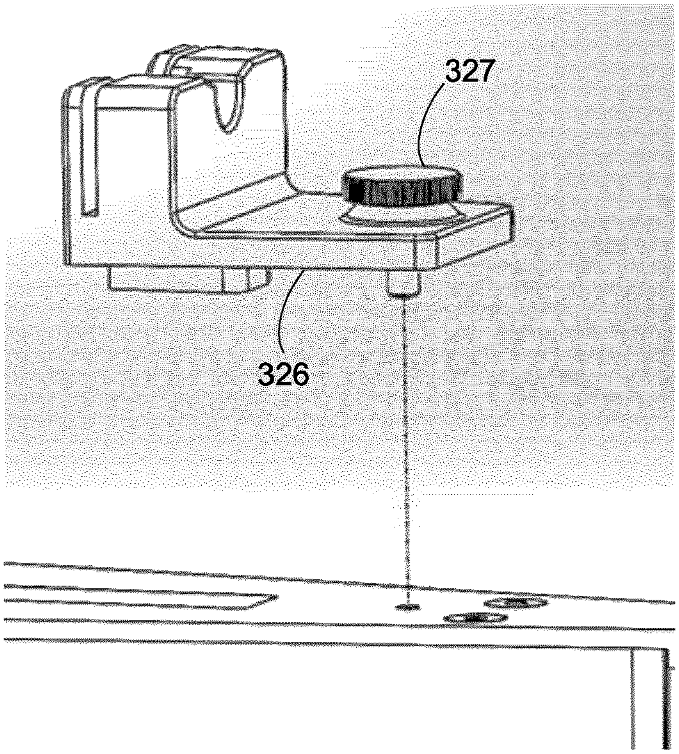
FIG. 3E illustrates an embodiment of the syringe retainer.
Figure 3F:
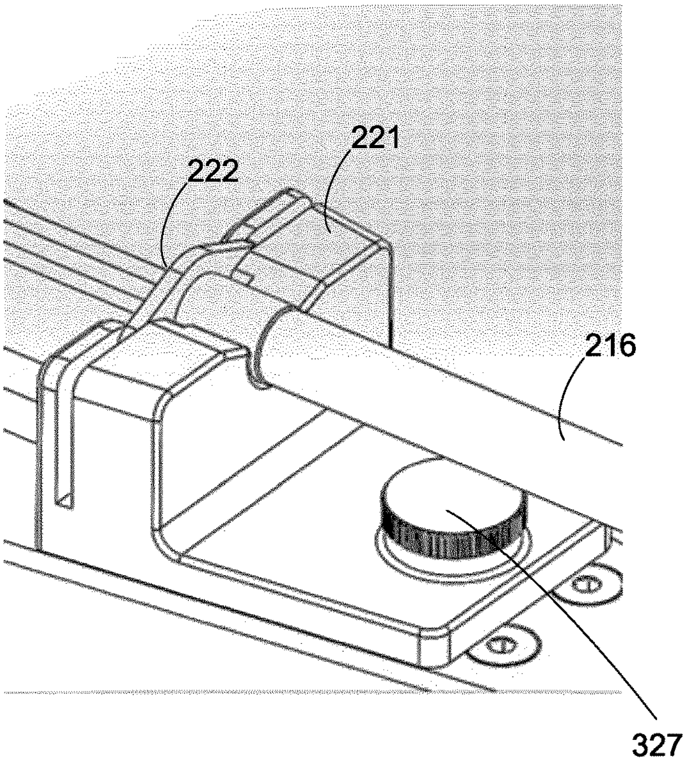
FIG. 3F illustrates an embodiment of the syringe retainer that is attached to a top of the syringe pump via the screw.

FIG. 3E illustrates another embodiment of the syringe retainer 326, which may include a semi-captive screw 327 that secures the syringe retainer 326 to the top 202 of the syringe pump 107. FIG. 3F illustrates an embodiment of the syringe retainer 326 that is attached to the top 202 of the syringe pump 107 via the screw 327. As illustrated in FIG. 3F, the syringe retainer 326 may be configured to hold the syringe barrel 216 of the syringe 108. Additionally, the syringe 108 may be snap-fit into the syringe retainer 326 via a notch defined by the syringe retainer 326. In certain embodiments, there may be various versions of the syringe retainer 326 including but not limited to, for example, 1 mL, 3 mL, and 5 mL versions of the syringe retainer 326.

Figure 4:
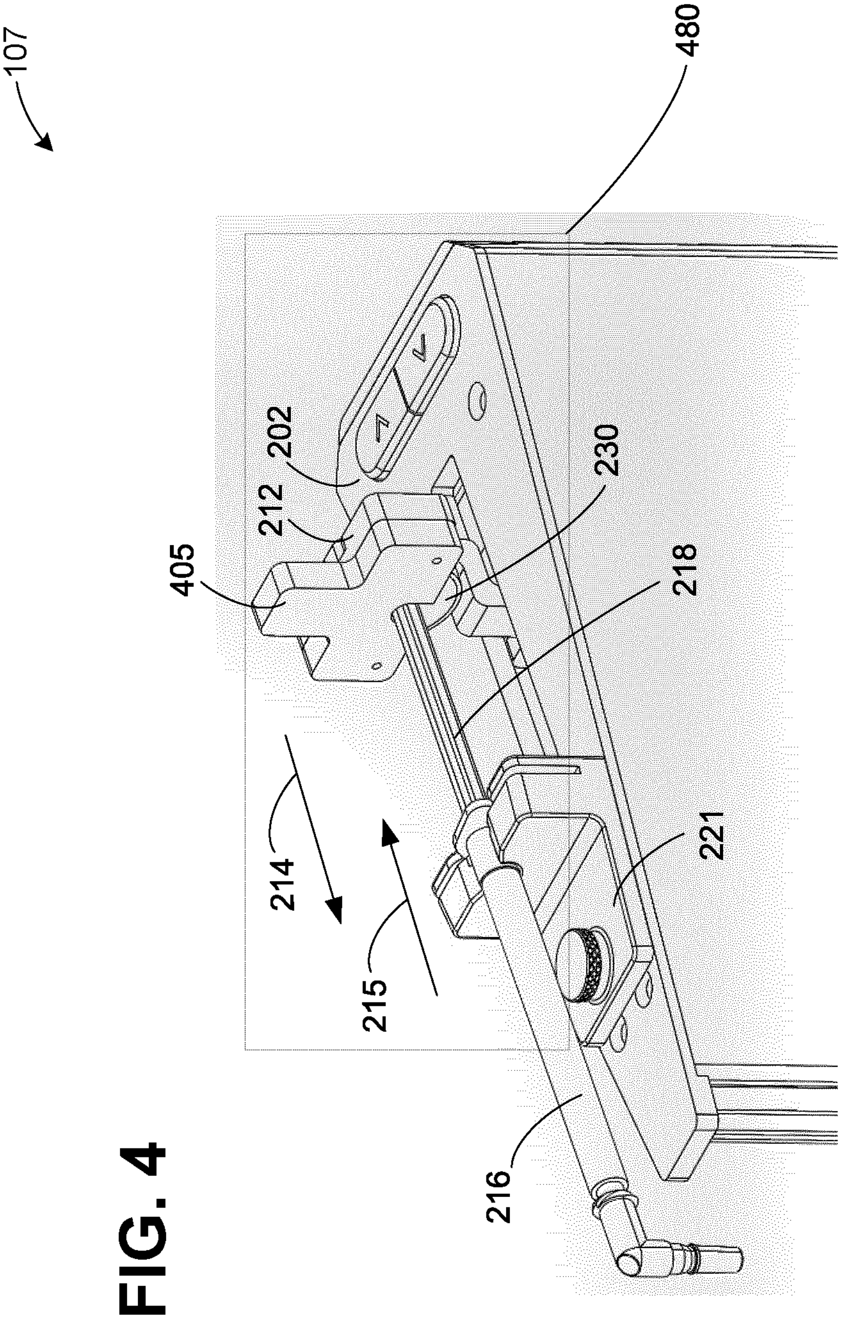
FIG. 4 is another image of the syringe pump of FIG. 2, with a plunger clip attached to the plunger driver and a portion of a plunger, to sandwich a plunger flange between the plunger clip and plunger cap/plunger driver.

Turning to FIG. 4, depicted is another illustration of syringe pump 107 with plunger clip 405 coupled to plunger driver 212 by way of the attachment elements 270 (not shown at FIG. 4 due to their view being obstructed by plunger clip 405). In embodiments, plunger clip 405 may be configured so as to surround at least a portion of plunger 218 and lock plunger flange 232 (not visible at FIG. 4 but see FIG. 2 and FIG. 3D) in position against the walls of plunger cap 230. In absence of plunger clip 405, it may be understood that plunger driver 212 may not be capable to draw plunger 218 out of syringe barrel 216 when plunger driver 212 is traveling in a reverse direction, exemplified by arrow 215. Via the use of plunger clip 405, plunger flange 232 becomes sandwiched between plunger cap 230 (and plunger driver 212) and plunger clip 405, such that it becomes possible to draw plunger 218 out of syringe barrel 216 when plunger driver 212 is traveling in the direction of arrow 215. It may be understood that plunger clip 405 may be used under circumstances where plunger driver 212 is traveling in the forward direction, exemplified by arrow 214, although its use is not strictly needed in such a use case.

While a single plunger clip 405 is shown, it may be understood that plunger clip 405 is one of a plurality of plunger clips that individually can be used with syringe pump 107 of the instant disclosure. Plunger clips may vary in dimensions such that different plunger clips can be used depending on the particular syringe being used, and specifically, based on the dimensions of the particular plunger. The plunger clips are such that specific plunger clips can be selected depending on the dimensions of the particular plunger/particular syringe being used, and in conjunction with appropriate syringe retainer (e.g., syringe retainer 121) and plunger cap 230, appropriate selection ensures that the center line of the syringe barrel is maintained substantially constant for syringes that hold different volumes (hence, have differing dimensions).

Figures 5A, 5B:
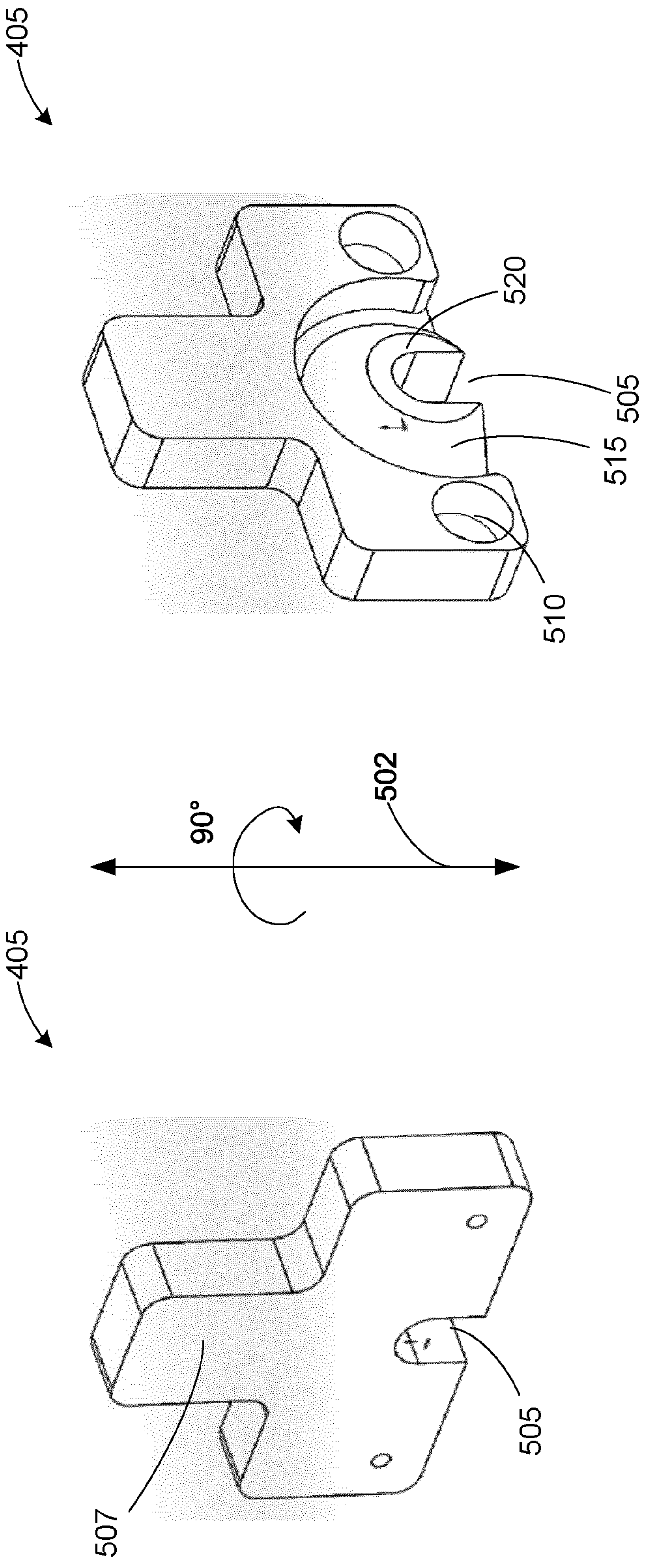
FIGS. 5A-5B are illustrations of the plunger clip depicted at FIG. 4 from two different angles.

Turning to FIGS. 5A and 5B, isolated illustrations of exemplary embodiments of plunger clip 405 are shown. Specifically, FIG. 5A represents an illustration of plunger clip 405 viewed from a substantially similar angle as that shown at FIG. 4, and FIG. 5B represents an illustration of the plunger clip of FIG. 5A rotated 90° about axis 502. As shown at FIG. 5A, plunger clip 405 has a T-shape, with a recess 505 (e.g., U-shaped) that is of a size and shape to fittingly receive a syringe plunger (e.g., plunger 218). A stem 507 of plunger clip 507 can serve as a means for grasping via a user, to facilitate a user's ability to physically couple the plunger clip 405 to the plunger and plunger driver (e.g., plunger driver 212).

Turning to FIG. 5B, depicted is another view of plunger clip 405 that illustrates cavities 510 capable to hold a means for attaching/securing plunger clip 405 to the plunger driver, by way of attachment means on the plunger driver (e.g., magnetic attachment means 270 at FIG. 2 and FIG. 3D). The recess 505 is viewable at FIG. 5B, and is formed in part via a convex portion 515, designed specifically to matingly engage with a concave portion of the plunger cap (e.g., plunger cap 230 at FIG. 2 and FIG. 3D). Although depicted as circularly concave, in other embodiments a cone-shaped portion can be used to matingly engage with an inverted cone-shaped portion corresponding to the plunger cap. Thus, broadly speaking the portion of plunger clip 405 that matingly engages with the plunger cap can be generally viewed as a male coupling portion, whereas the portion of the plunger cap that receives the male coupling portion can be generally viewed as a female coupling portion. A portion of plunger clip 405 that forms the recess 505 includes flat edge section 520, to abut up against a plunger flange (e.g., plunger flange 232 at FIG. 2 and FIG. 3D).

Figure 5C:
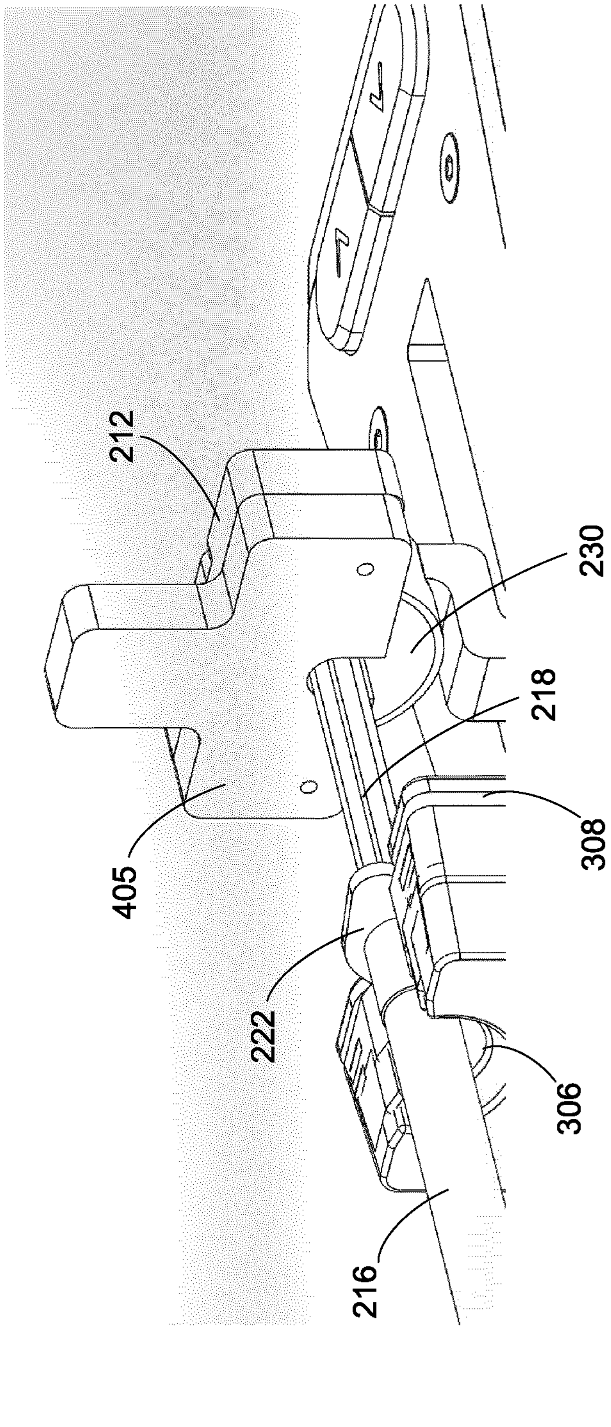
FIG. 5C depicts a close up illustration of a portion of the syringe pump depicted at FIG. 4.

Turning to FIG. 5C, depicted is a close-up view of the region of syringe pump 107 defined by dashed box 480 at FIG. 4, to clearly illustrate a syringe barrel 216 received by recess 306, where syringe barrel flange 222 is sandwiched between walls of the crevasse 308 of syringe retainer 221. FIG. 5C is shown to further clearly illustrate plunger clip 405 coupled to plunger driver 212, and fittingly engaged with at least a portion of plunger 218, thereby sandwiching plunger flange (e.g., plunger flange 232 at FIG. 2 and FIG. 3D) between plunger clip 405 and plunger cap 230/plunger driver 212.

Figure 5D:
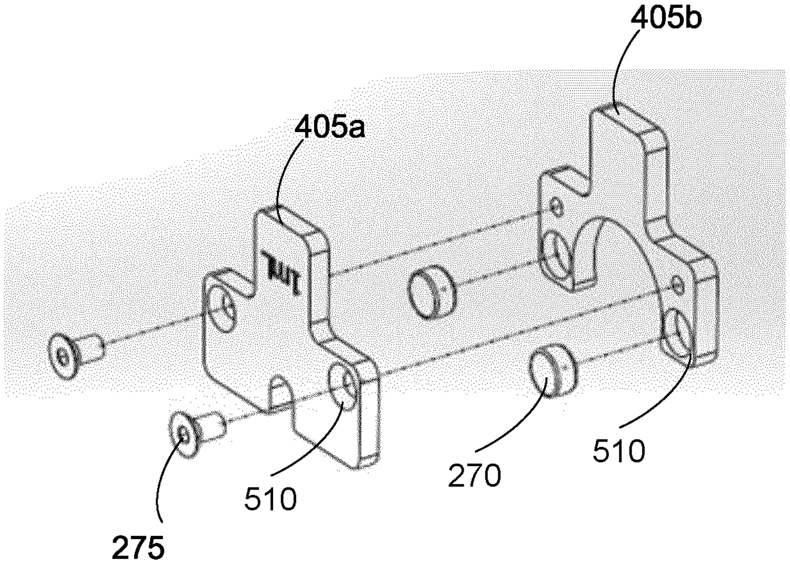
FIGS. 5D-5G illustrate additional embodiments of the plunger clip and plunger cap comprising magnetic attachments.
Figure 5E:
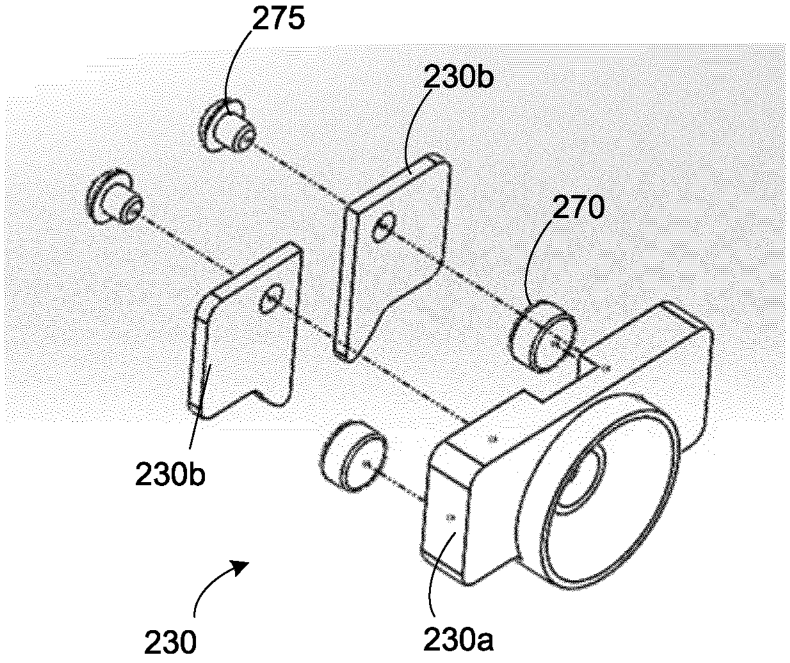
Figure 5F:
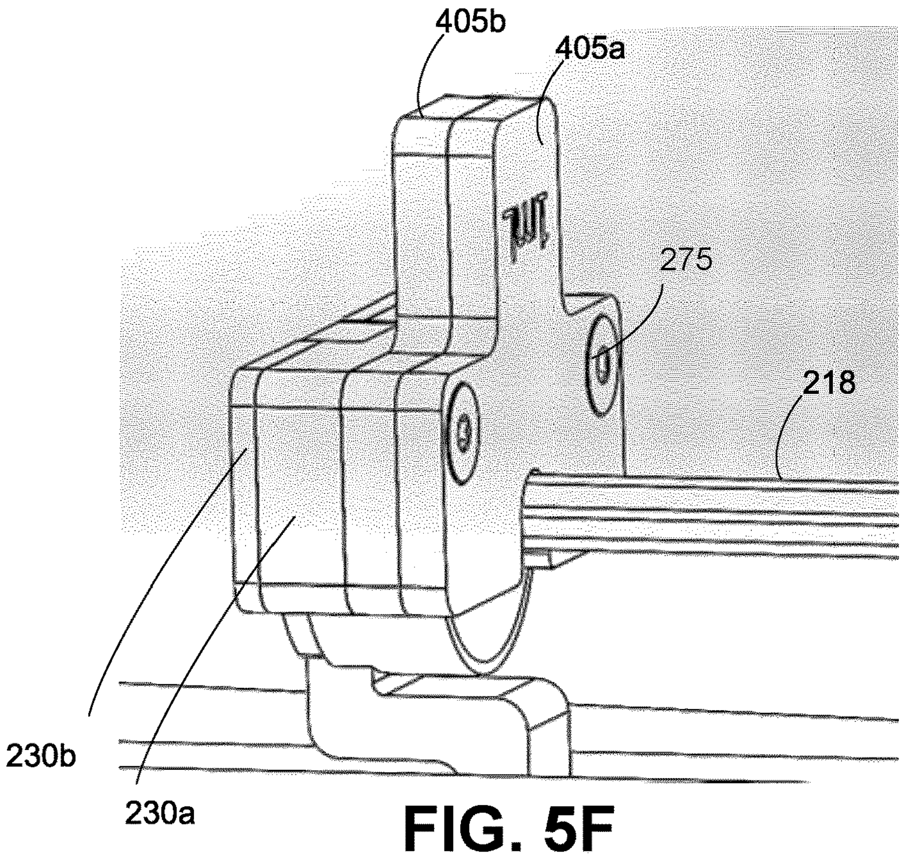
Figure 5G:
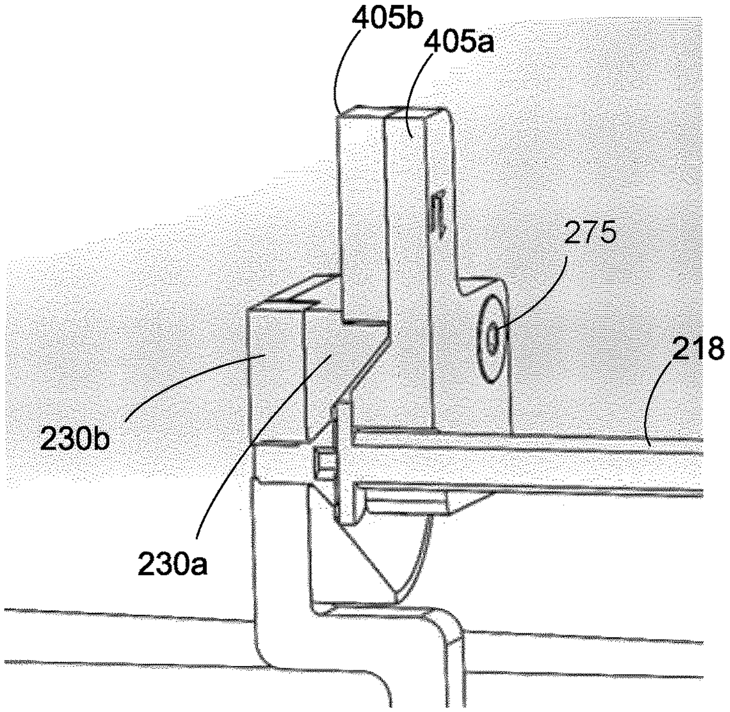

FIGS. 5D-5G illustrate additional embodiments of the plunger clip 405 and plunger cap 230 configured to hold magnets 270 enclosed in cavities contained therein so as to physically sandwich the installed syringe, which provides the ability to pull up on the syringe as well as press down the syringe. For example, FIG. 5D illustrates plunger clip 405 comprising a front plate 405*a* and back plate 405*b* attached by screws 275 and enclosing two magnets 270 for magnetic attachment to the plunger cap. As illustrated in FIG. 5F, in certain embodiments, the plunger cap 230 may also comprise a front plate 230*a* and a back plate 408*b* attached by screws 275 and enclosing two magnets 270 to magnetically attach to the plunger clip. As such, in certain embodiments, the plunger clip 405 and/or plunger cap 230 can be configured to hold magnets enclosed in cavities contained therein. Thus, as illustrated in FIGS. 5F and 5G, the plunger clip 405 illustrated in FIG. 5D and the plunger cap 230 illustrated in FIG. 5E may be magnetically attached, thereby enclosing the plunger driver 212 between the plunger cap 230 and the plunger clip 405 with the plunger 218 positioned in a recess of the plunger clip 405.

Figure 5H:
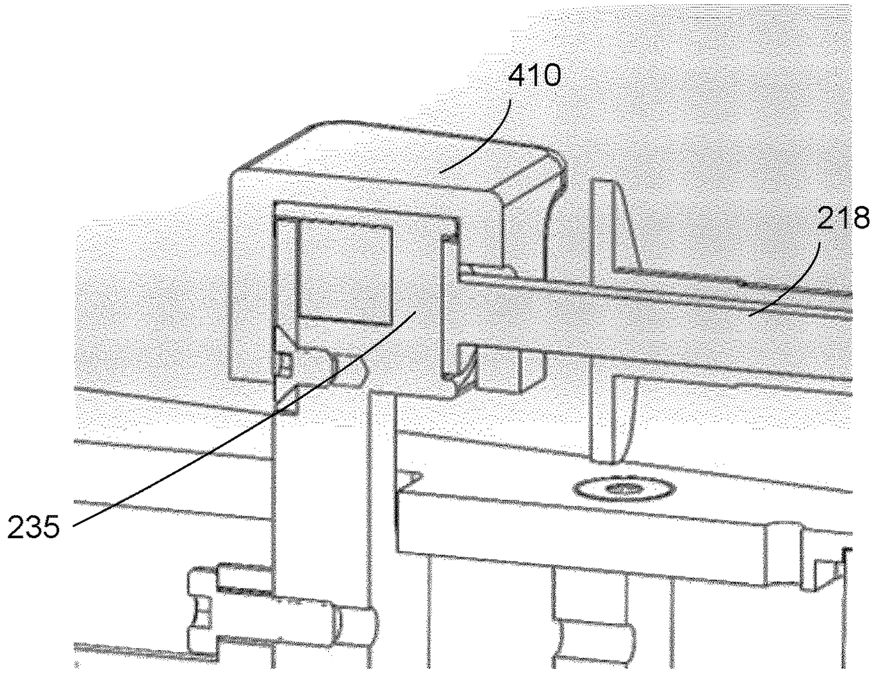
FIGS. 5H-5J illustrate another embodiment of the plunger clip, according to certain embodiments.
Figure 5I:
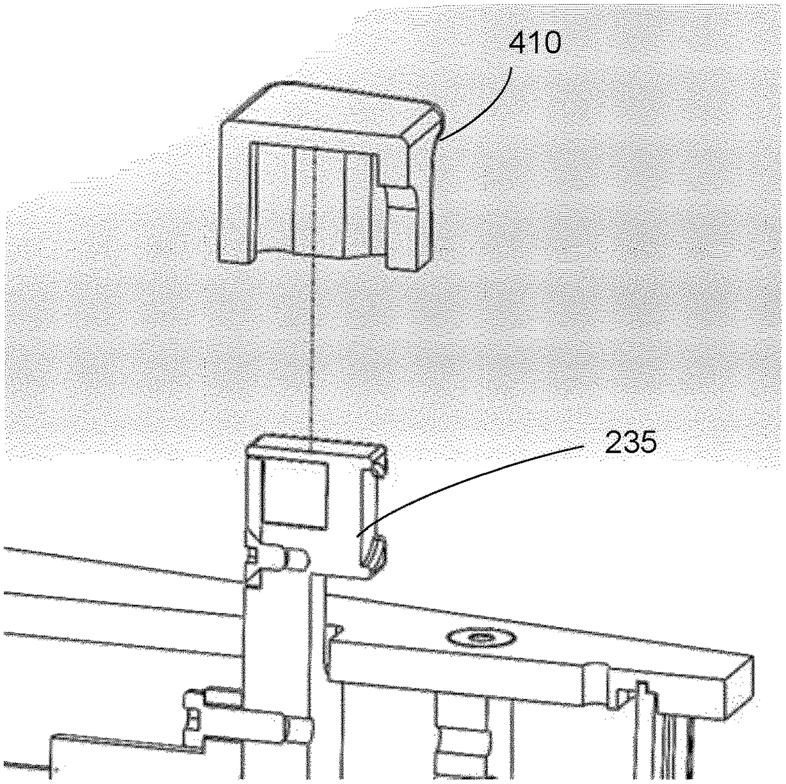
Figure 5J:
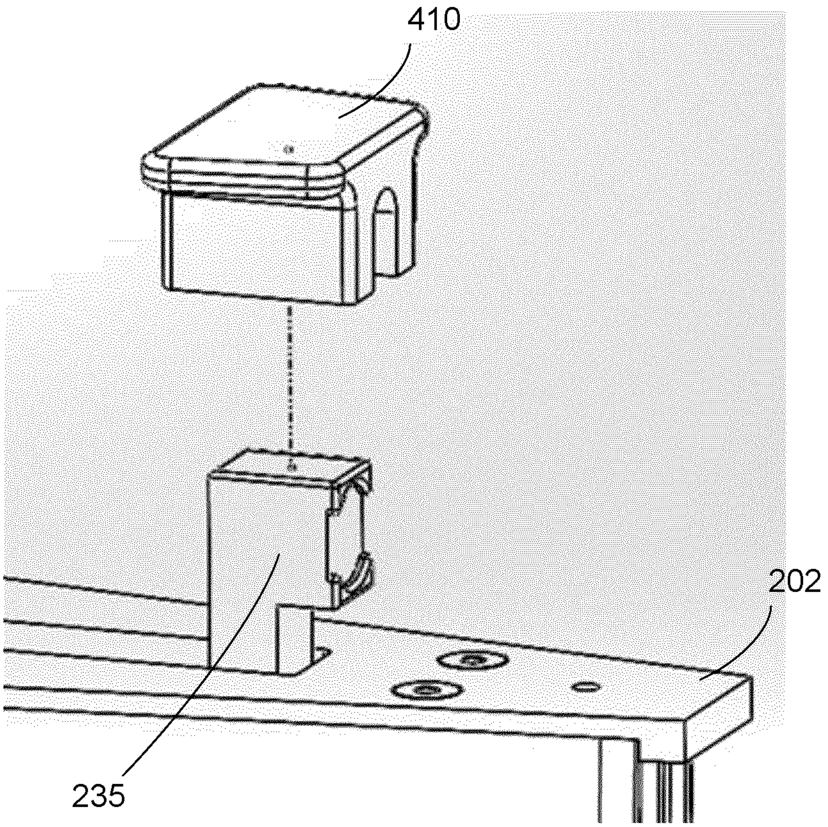

FIGS. 5H-5J illustrate alternative embodiments of the plunger clip and plunger cap 230 for use, e.g., with a direct insertion syringe. For example, FIGS. 5H-5J illustrate a plunger clip 410 that functions slightly different compared to the plunger clip 405. According to some embodiments, the syringe cap 235 may have a magnet installed in its head. In some embodiments, the plunger clip 410 may be made of steel so that it may be magnetically attracted to the magnet in the head of the plunger cap 235.

Via the combined use of a syringe retainer capable to fittingly receive syringe barrels of different dimensions, and a plunger cap configured with a concave or inverted cone shape, syringe pumps of the present disclosure advantageously maintain a center line constant between syringes of different dimensions. For example, the center line of a 1 ml syringe would be substantially the same as the center line of a 5 ml syringe. Similar logic applies to syringes of other dimensions. Maintenance of the center line between syringes of different dimensions advantageously serves to minimize variation in terms of internal volume between multiple syringes used in conjunction with printing system 100.

Figure 6A:
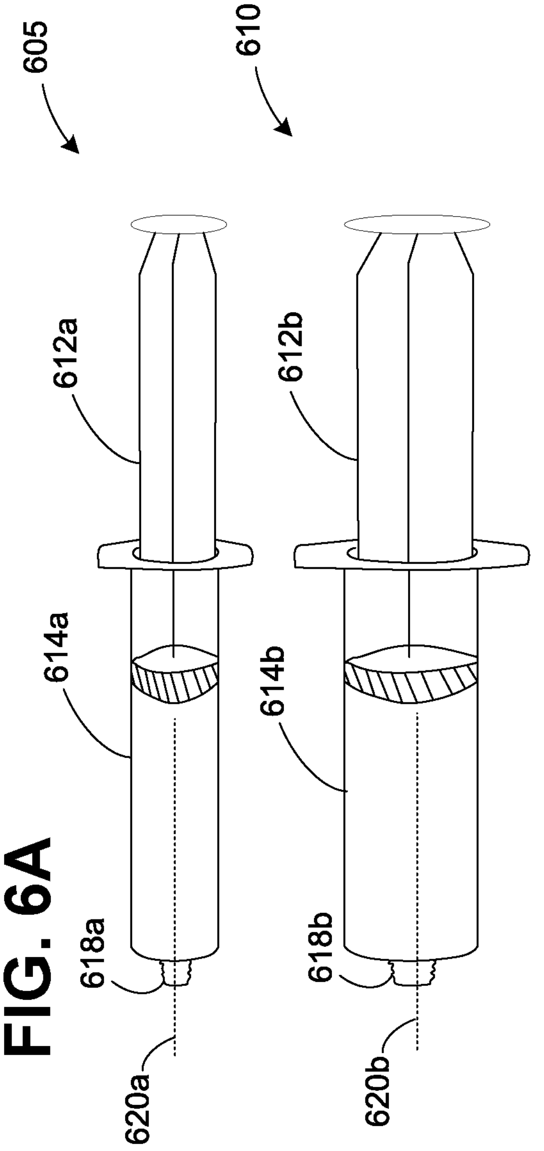
FIGS. 6A-6B are illustrations depicting how a center line of syringes of varying diameters can be maintained constant according to aspects of the present disclosure.

Specifically, turning to FIG. 6A, depicted is a first syringe 605 and a second syringe 610. Each syringe is comprised of a plunger (612*a* and 612*b*), and a syringe barrel (614*a* and 614*b*). In this example, each of said syringes include a female luer (618*a* and 618*b*) associated with respective syringe barrels. As can be seen visually, syringe barrel 614*a* of first syringe 605 is of a smaller diameter than syringe barrel 614*b* of second syringe 610. Each syringe has a central longitudinal axis (620*a* and 620*b*), or center line, along a length of the respective syringe, the central longitudinal axis being an axis equidistant from walls of the syringe barrel.

Figure 6B:
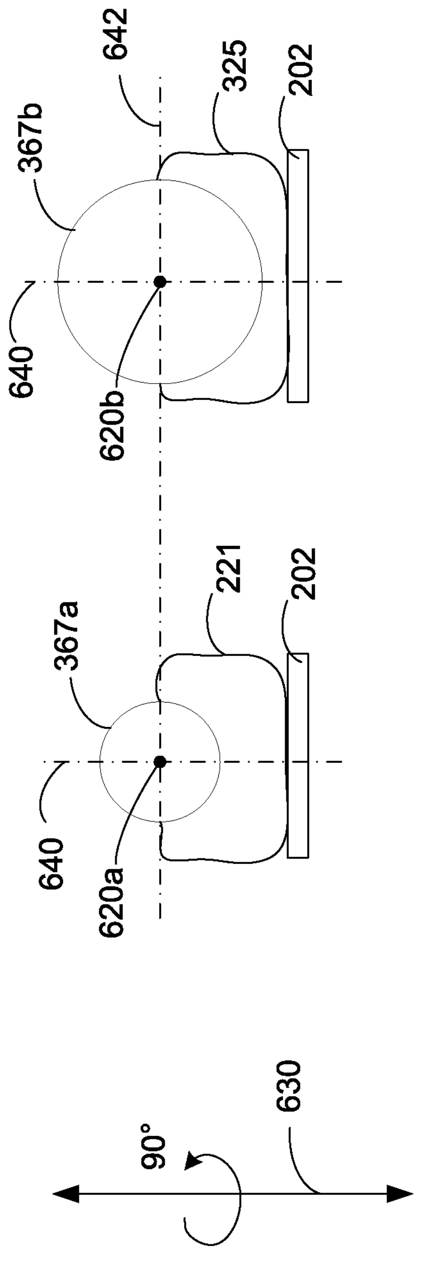

FIG. 6B shows the syringes of FIG. 6A rotated 90° about vertical axis 630, where first syringe 605 is received by syringe retainer 221, and second syringe 610 is received by syringe retainer 325. Each of syringe retainer 221 and syringe retainer 325 are secured to top 202 of syringe pump 107. As illustrated via the use of the different syringe retainers, the center line is maintained constant with respect to top 202 of syringe pump 107, in terms of vertical 640 and horizontal 642 axes. It may be understood that in this example, vertical, and horizontal are relative terms, where the vertical axis 640 is described as perpendicular to top 202 of syringe pump 107, and the horizontal axis 642 is described as parallel to top 202 of syringe pump 107.

Figure 7:
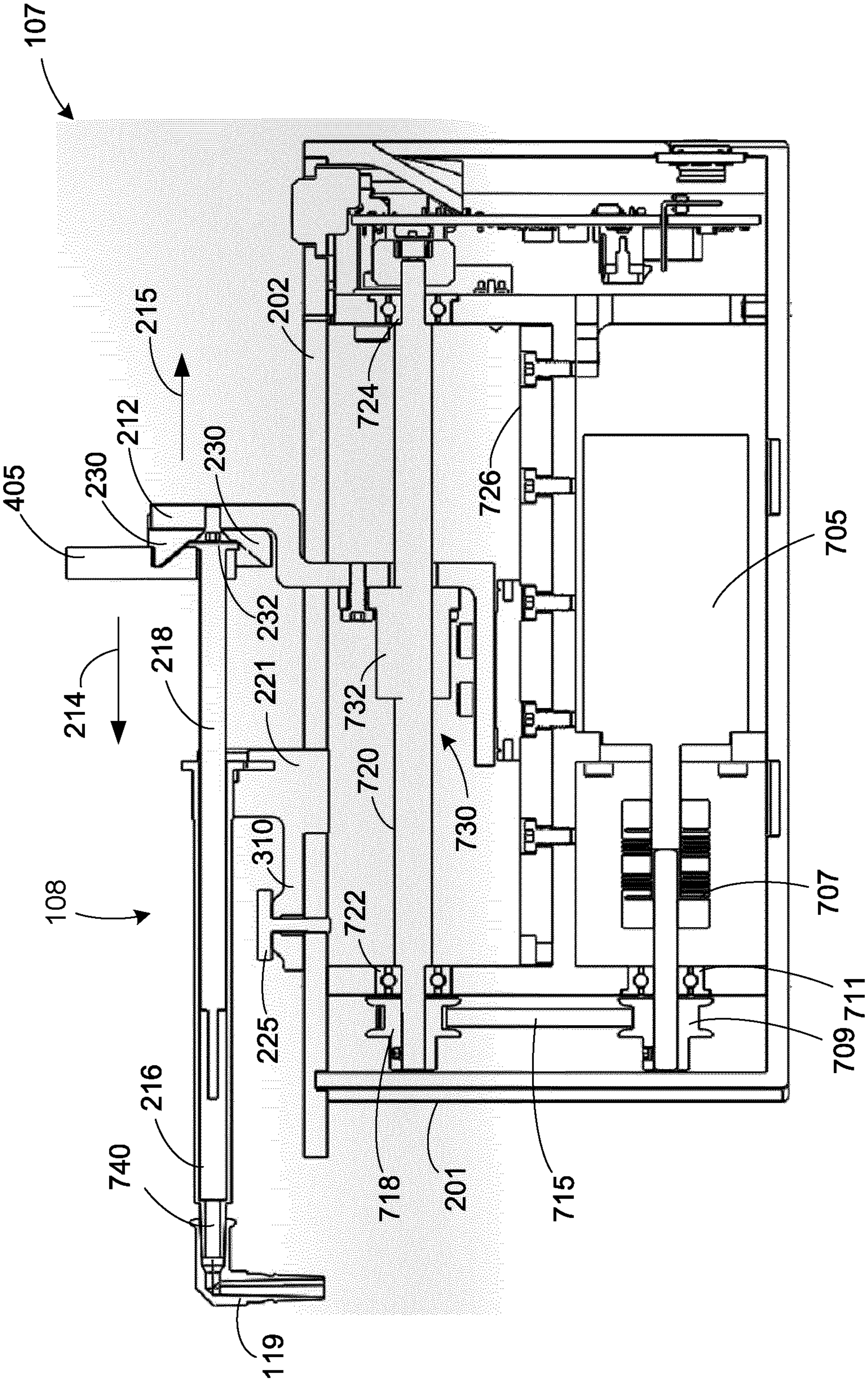
FIG. 7 is a transparent rendering of the syringe pump of FIG. 2 from a side-view to illustrate various aspects of the syringe pump.

Turning to FIG. 7, depicted is a transparent side view of syringe pump 107. The inner workings of syringe pump 107 are shown for reference, but it may be understood that other design options are within the scope of this disclosure.

Syringe pump 107 includes housing 201. In exemplary embodiments, a wedge-shape housing is provided, such that a plurality of such syringe pumps can be positioned in a radial array between 15 and 60 degrees relative to one another on mounting bracket 106 of printing system 100. Within said housing, syringe pump 107 includes stepper motor 705. Stepper motor 705 is coupled to a flexible coupling 707, which is in turn coupled to lower pulley 709 by way of a first support bearing 711. A drive belt 715 couples lower pulley 709 to upper pulley 718. Upper pulley 718 is in turn coupled to lead screw 720. Lead screw 720 is coupled to a second support bearing 722, and a third support bearing 724.

Syringe pump 107 further comprises a guide rail 726, and a sliding block assembly 730 comprising ball nut 732. Rotational motion of the lead screw 720 induced by way of drive belt 715 via operation of stepper motor 705 produces linear movement of ball nut 732 and in turn linear movement of the sliding block assembly 730 along the length of lead screw 720 and guide rail 726. A portion of sliding block assembly 730 extends through the slot (not shown at FIG. 7 but see slot 210 at FIG. 2) on the top 202 of syringe pump 107, to form the plunger driver 212 operative to drive plunger 218 into syringe barrel 216 of syringe 108.

Syringe barrel 216 is secured via syringe retainer 221 as discussed above. As shown at FIG. 7, screw 225 extends through shelf 310 of syringe retainer 221 and into top 202 of syringe pump 107, to secure syringe retainer 221 to the top 202 of syringe pump 107. Shown for illustrative purposes is elbow shaped connector 119 coupled to tip 740 of syringe 108.

Returning to the plunger driver 212, adjacent the plunger driver 212 is plunger cap 230, configured to receive plunger flange 232. From the transparent side-view depicted at FIG. 7, it can be seen that plunger flange 232 abuts up against walls of plunger cap 230. In some embodiments, syringe pump 107 includes a plunger clip 405. In embodiments, plunger clip 405 attaches to plunger driver 212 by way of magnetic attachment means 270 (shown at FIGS. 2, 3D and 5D-5G. In embodiments, plunger clip 405 may be configured so as to surround at least a portion of plunger 218 and secure plunger flange 232 in position against the walls of plunger cap 230. As discussed, in absence of plunger clip 405, plunger driver 212 may not be capable to draw plunger 218 out of syringe barrel 216 when plunger driver 212 is traveling in a reverse direction, exemplified by arrow 215.

Via the use of plunger clip 405, plunger flange 232 becomes sandwiched between plunger cap 230 and plunger clip 405, such that it becomes possible to draw plunger 218 out of syringe barrel 216 when plunger driver 212 is traveling in the direction of arrow 215.

Print Heads and Adaptors:

As discussed above with regard to FIG. 1A, printing systems of the present disclosure are configured to receive one or more print heads and, in embodiments, one or more adaptors. Other aspects and components associated therewith will become clear upon further elaboration of the detailed description below.

Figure 8:
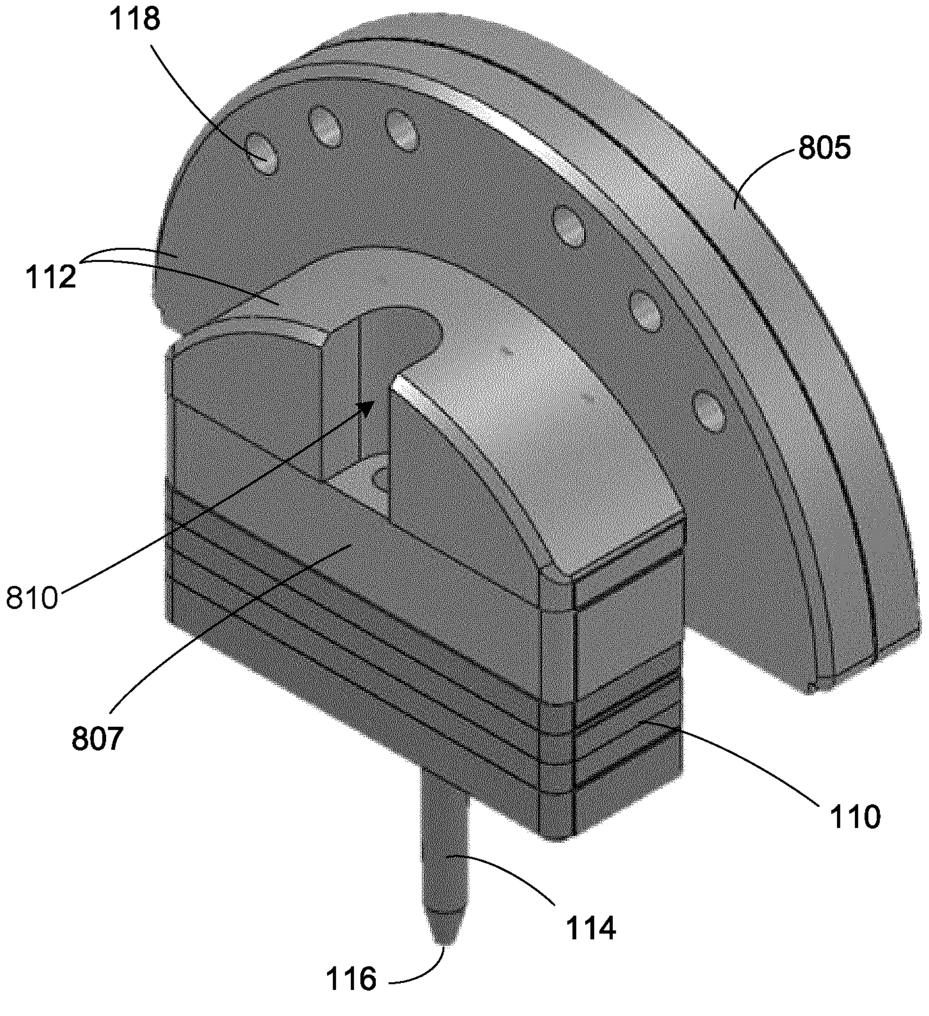
FIG. 8 illustrates an embodiment of an adaptor, print head, and back plate for use in conjunction with the microfluidic printing system of FIG. 1A.

Turning now to FIG. 8, depicted is one embodiment of an adaptor and print head of the present disclosure. With reference to FIG. 8, the adaptor and print head are substantially similar to those discussed with reference to FIG. 1A, and accordingly, FIG. 8 refers to adaptor 112 and print head 110. Adaptor 112 includes a plurality of syringe inlets 118, capable to receive material flow from one or more syringes attached to one or more syringe pumps (e.g., syringe pump 107), where said syringe pumps are attached to a mounting bracket (e.g., mounting bracket 106) of a printing system (e.g., printing system 100) of the present disclosure. In such an embodiment, material flow may be routed, via the microfluidic adaptor channels to the print head 110, which houses a plurality of fluid inlets configured to receive material flow from the microfluidic adaptor channels associated with the adaptor 112, and a plurality of microfluidic printing channels corresponding to said plurality of fluid inlets, where the microfluidic printing channels in the print head 110 merge into a single dispensing channel 114 leading to dispensing orifice 116 as discussed.

In embodiments, a back plate 805 is configured to couple to adaptor 112. In some embodiments, back plate 805 may be configured to provide pneumatic inlets positioned in a manner so as to enable pneumatic control of one or more valves associated with said microfluidic adaptor channels and/or microfluidic printing channels. In additional or alternative embodiments, one or more of the microfluidic adaptor channels and/or microfluidic printing channels may include valves that are passively actuated, for example one-way valves that open responsive to pressure of a material flow exceeding a valve-opening threshold, and which are incapable of enabling fluid flow in an opposite direction to that capable of opening said valve.

In some embodiments, all of the valves associated with one or more microfluidic adaptor channels and/or microfluidic printing channels are passively actuatable (e.g., duckbill valves, one-way check valves), and in such an example, back plate 805 may merely serve as a mounting bracket, or may not be needed altogether. In some embodiments, a valve layer 807 comprises part of adaptor 112, or part of print head 110. In embodiments, one or more microfluidic channels included in valve layer 807 may include a valve as discussed, although it is within the scope of this disclosure that valve placement can additionally or alternatively be included outside of valve layer 807.

In some embodiments, adaptor 112 includes a recessed section 810, which can enable a direct insertion of a syringe (see, e.g., syringe 120 at FIG. 1A) attached to a syringe pump (e.g., syringe pump 107) to a fluid inlet of the print head 110, thus bypassing the adaptor (e.g., adaptor 112) and corresponding syringe inlets (e.g., syringe inlets 118) associated with the adaptor.

Figure 9B:
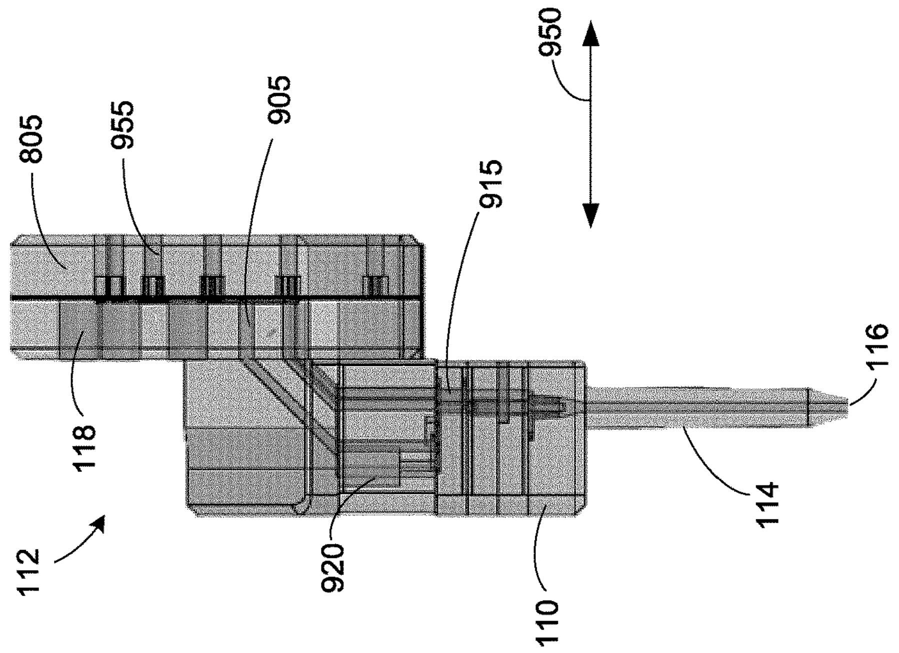
FIGS. 9A-9B depict transparent illustrations of the adaptor, print head, and back plate of FIG. 8, from a front view (FIG. 9A) and a side-view (FIG. 9B).
Figure 9A:
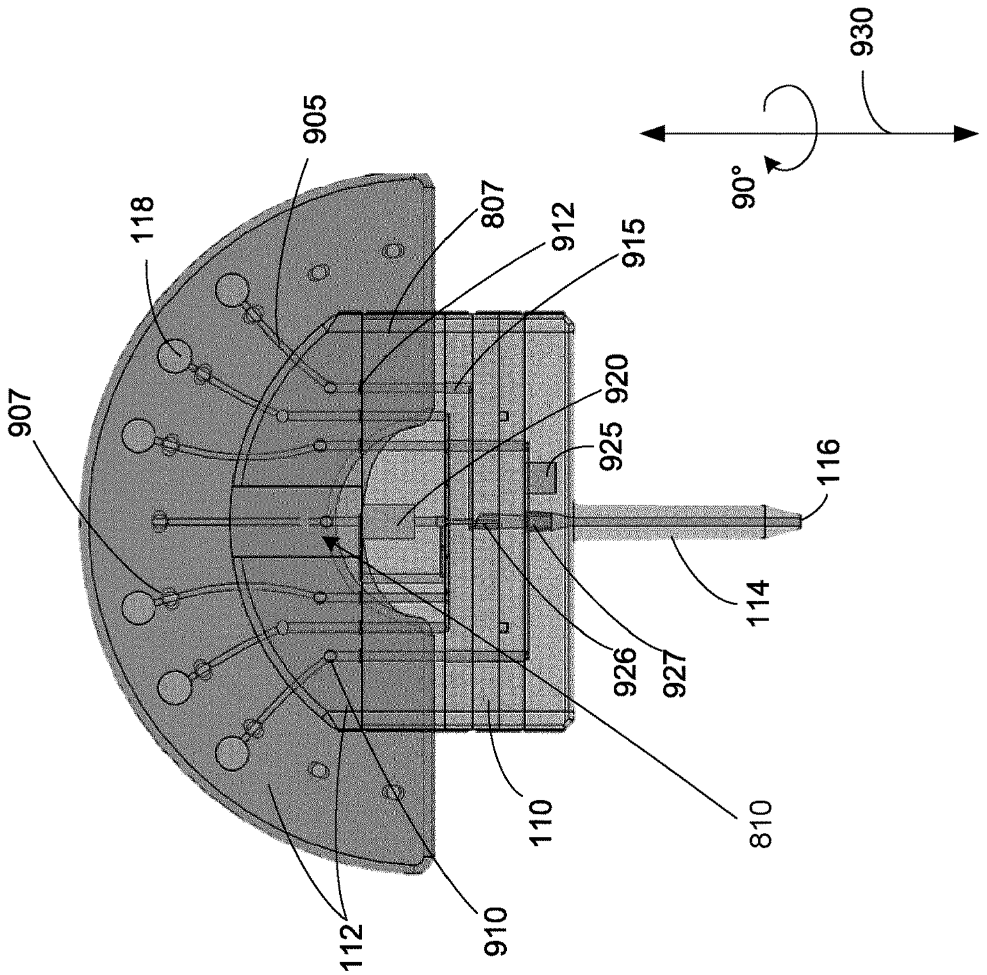

Turning to FIG. 9A, depicted is a transparent front view of adaptor 112 coupled to print head 110. Illustrated are the plurality of syringe inlets 118 coupled to microfluidic adaptor channels 905. Included as part of the microfluidic adaptor channels 905 of adaptor 112 are valves 907, which as discussed may be passive or pneumatically actuated. The embodiment shown at FIG. 9A additionally includes valve layer 807, which is discussed in this example illustration as comprising part of print head 110. Microfluidic adaptor channels 905 couple to fluid inlets 912 associated with print head 110. Print head 110 includes a plurality of microfluidic channels 915, each stemming from respective fluid inlets 912.

As discussed, in some embodiments, adaptor 112 includes a recessed section 810, to enable a direct insertion of a syringe to print head 110, and specifically to direct syringe inlet 920, which is in turn coupled to one of the plurality of microfluidic printing channels 915, specifically one that stems from direct syringe inlet 920. In exemplary embodiments, the corresponding microfluidic printing channel may further comprise an extra-large valve, e.g. for cell clusters, larger cells, and the like.

The plurality of microfluidic printing channels 915 in turn merge within print head 110 into single dispensing channel 114, leading to dispensing orifice 116. In embodiments direct syringe inlet may be used for materials that contain biological material, for example cells. Although not specifically shown, in embodiments a valve may be used to control flow of said biological material out of direct syringe inlet 920.

In embodiments, print head 110 includes an image 925, e.g., a machine-readable image. In embodiments, the image comprises a code (e.g., two dimensional bar code such as a QR code, microQR code, a one-dimensional bar code, an alphanumeric label, and the like) which can be scanned by a camera associated with printing systems (e.g., printing system 100) of the present disclosure. Information stored in the code can then be extracted, for example via a computing device associated with a control system (e.g., control system 102) and correspondingly used.

For example, the information stored as part of the image may include detailed information on one or more of dimensions of the print head, number of fluid inlets fluidically coupled in turn to microfluidic channels, spacing of said fluid inlets in relation to one another, and the like. A computing device (e.g., computer associated with control system 102 at FIG. 1A) may extract the coded information and in turn, produce an output relating to the extracted information. In one example, the output may include instructions capable of being interpreted by a user of the printing system, as to where one or more syringe pumps (e.g., syringe pump 107), and corresponding syringe (e.g., syringe 108 at FIG. 1A) should be placed. In some embodiments, the instructions may be in the form of a visual alert, for example text and/or one or more images, viewable on a computer (e.g., computer associated with control system 102 at FIG. 1A), or in some other way. For example, in embodiments the instructions can be viewed a device such as a smartphone, tablet, and the like communicatively coupled to the printing system (e.g., connected over the internet, emailed to a user email account, and the like). Additionally or alternatively, the visual alert may be based on one or more lights, for example one or more lights included as part of the mounting bracket (e.g., mounting bracket 106 at FIG. 1A).

For example, depending on the particular mounting bracket, there may be between 3 and 11 locations (i.e. syringe bays) where syringe pumps (e.g., wedge-shaped syringe pumps of the present disclosure) can be attached thereto. In embodiments, each of said locations may be associated with a light. The lights can all be of one particular color, brightness, size, shape, and the like, or the lights may be different between said locations. Upon extraction of the instructions from the image associated with the particular print head coupled to the printing system, a command may be send via the controller (e.g., controller 103 at FIG. 1A) to activate one or more lights associated with the different locations where syringe pumps can be attached. The locations in which a light is turned on may correspond to those locations where a syringe pump should be attached thereto. In this way, a user may be readily alerted as to what particular bays the syringe pumps should be attached on the mounting bracket, for use with a specific print head. Accordingly, print heads that can be used with the printing systems herein disclosed may in some embodiments require syringe pumps to be attached to all available syringe bays on the mounting structure (e.g., 11 out of 11 locations), or may in other examples require syringe pumps to be attached to a fraction (e.g., 5 of 11, or 3 of 7, etc.) of the syringe bays.

Turning to FIG. 9B, depicted is a transparent side view of print head 110 coupled to adaptor 112, and back plate 805. In other words, FIG. 9B represents the illustration of FIG. 9A rotated 90° about vertical axis 930 depicted at FIG. 9A. Viewable from this transparent side view are syringe inlets 118, microfluidic adaptor channels 905, microfluidic printing channels 915, dispensing channel 114, and dispensing orifice 116. Also viewable is direct syringe inlet 920. In some embodiments, as depicted at FIG. 9B, microfluidic adaptor channels 905 traverse through at least a portion of adaptor 112 at an angle. The angle illustrated at FIG. 9B is an approximately 45° angle with respect to horizontal axis 950 shown at FIG. 9B, but other angles are within the scope of this disclosure. For example, microfluidic channels 905 may traverse through second portion at an angle of anywhere between 20° and 60° with respect to horizontal axis 950, such as about 20°, or about 25°, or about 30°, or about 35°, or about 40°, or about 45°, or about 50°, or about 55°, or about 60°.

Also viewable at FIG. 9B are pneumatic inlets 955. Pneumatic inlets 955 are included as part of back plate 805. Specifically, in the depicted embodiment valves 907 (not viewable at FIG. 9B but refer to FIG. 9A) are included within microfluidic adaptor channels 905, and comprise valves that are pneumatically actuatable, hence back plate 805 includes the pneumatic inlets 955 appropriately positioned with respect to said valves, so as to deliver compressed air or compressed inert gas to said valves for control thereof.

Figure 10:
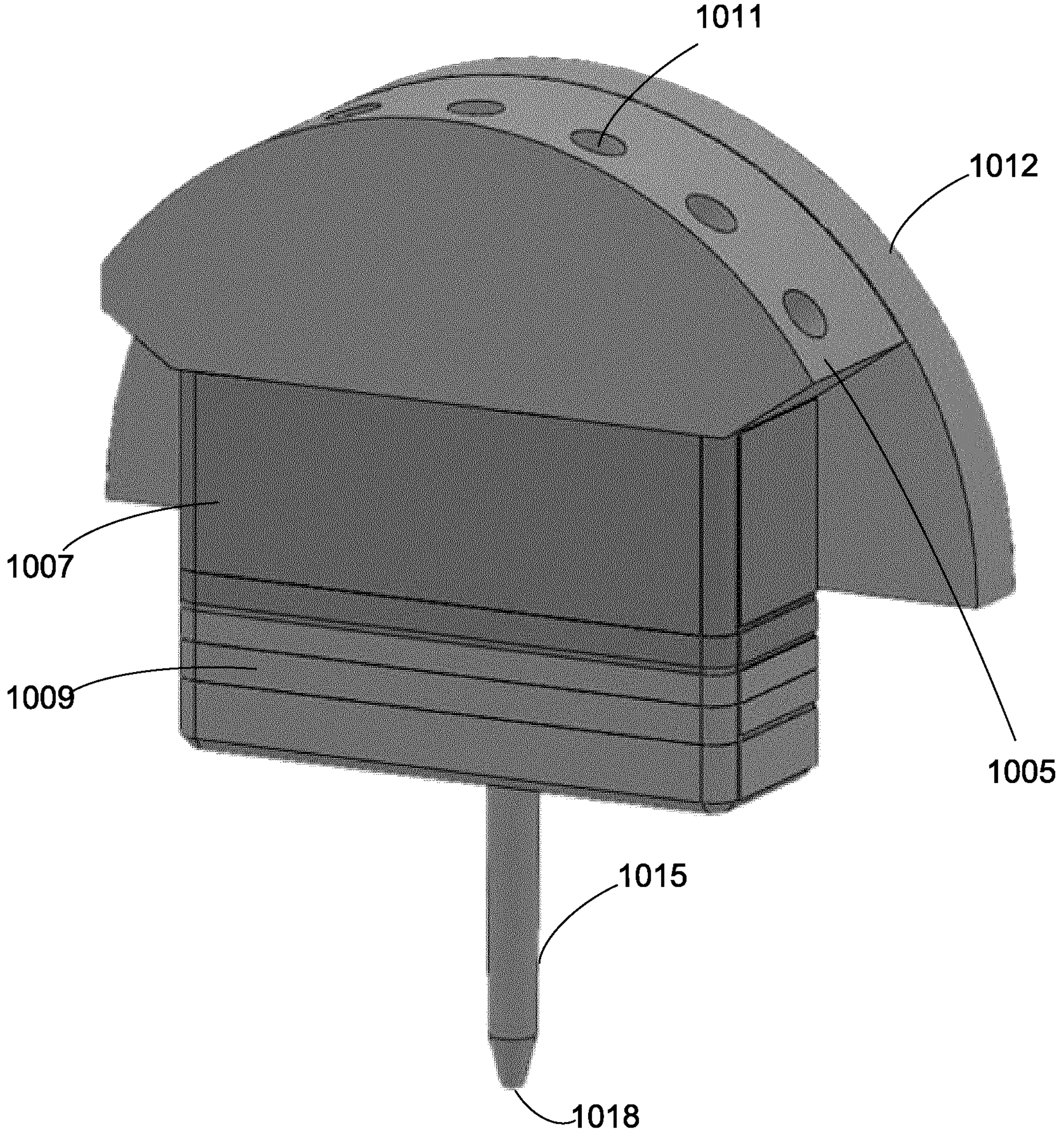
FIG. 10 illustrates another embodiment of an adaptor, print head, and back plate for use in conjunction with the microfluidic printing system of FIG. 1A.
Figure 11A:
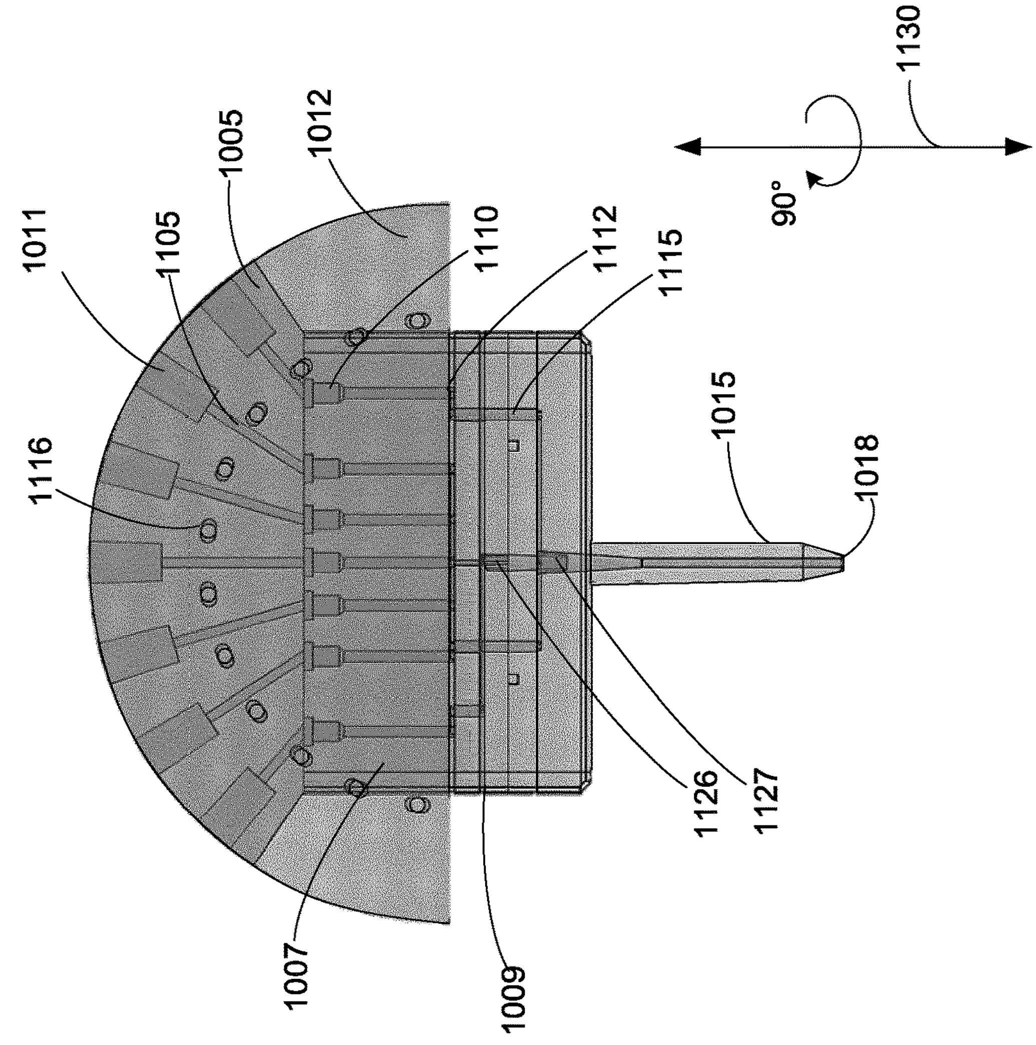
FIGS. 11A-11B depict transparent illustrations of the adaptor, print head, and back plate of FIG. 7, from a front view (FIG. 8A) and a side-view (FIG. 8B).
Figure 11B:
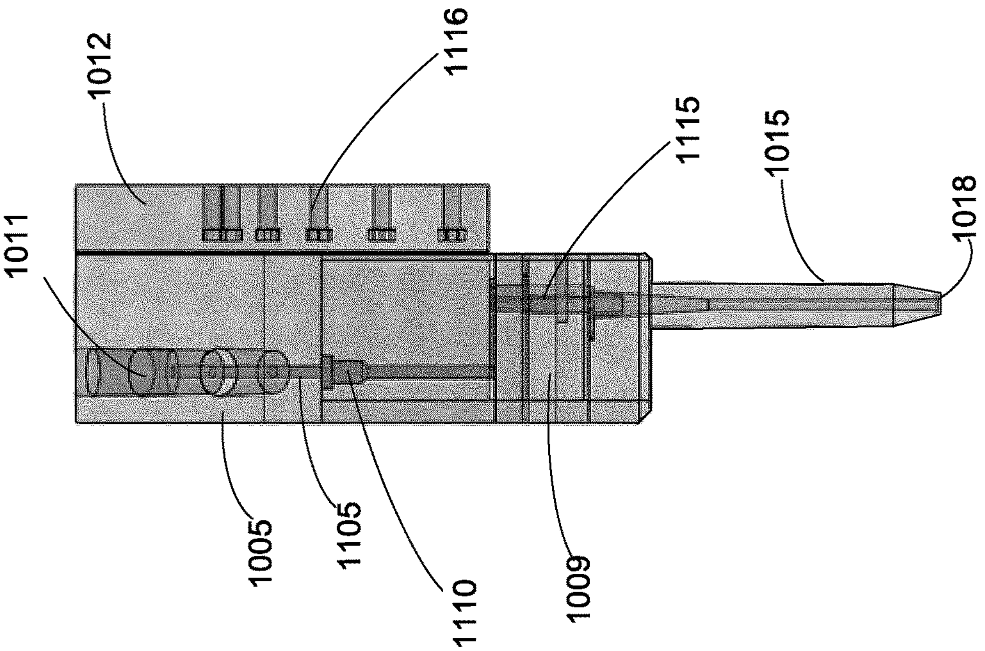

Turning now to FIG. 10, depicted is another embodiment of an adaptor and print head relevant to the present disclosure. The adaptor and print head depicted at FIG. 10, and further illustrated at FIGS. 11A-11B are different than the adaptor and print head discussed with regard to FIG. 8 and FIGS. 9A-9B. Accordingly, although some aspects are similar between the different adaptors and print heads, different numerals are used to describe the features for clarity.

FIG. 10 illustrates adaptor 1005 positioned atop print head 1009. Adaptor 1005 comprises a plurality of syringe inlets 1011, capable to receive material flow from one or more syringes attached to one or more syringe pumps (e.g., syringe pump 107), where said syringe pumps are attached to a mounting bracket (e.g., mounting bracket 106) of a printing system (e.g., printing system 100) of the present disclosure. In such an embodiment, material flow may be routed, via microfluidic adaptor channels, through adaptor 1005, and routed to the print head 1009, which houses a plurality of fluid inlets configured to receive material flow from said microfluidic adaptor channels. Print head 1009 further includes a plurality of microfluidic printing channels corresponding to said plurality of fluid inlets, where the microfluidic printing channels in the print head 1009 merge into a single dispensing channel 1015 leading to dispensing orifice 1018.

In embodiments of the adaptor and print head of FIG. 10, included is a valve layer 1007 which comprises part of adaptor 1005, or part of print head 1009. In embodiments, one or more microfluidic channels included in valve layer 807 may include a valve (e.g., passively or pneumatically actuated), although it is within the scope of this disclosure that valve placement can additionally or alternatively be included outside of valve layer 1007.

Depicted at FIG. 10 is back plate 1012. Back plate 1012 may be capable to attach to adaptor 1005, to assist in mounting of the adaptor 1005 to a printing system of the present disclosure (e.g., printing system 100 at FIG. 1A). In embodiments where all of the valves included as part of the microfluidic inlet channels are passively actuated, back plate may simply be used for mounting purposes. However, it is within the scope of this disclosure that in some embodiments, back plate 1012 can include pneumatic inlets positioned in a manner so as to enable pneumatic control of the valves associated with said microfluidic inlet channels.

Turning now to FIG. 11A, depicted is a transparent front view of adaptor 1005, coupled to print head 1009. Also viewable is back plate 1012. Illustrated are the plurality of syringe inlets 1011 coupled to microfluidic adaptor channels 1105. In this depicted embodiment, valve layer 1007 is discussed as being part of adaptor 1005. As shown, each of the microfluidic adaptor channels 1105 include valves 1110. Microfluidic adaptor channels 1105 couple to fluid inlets 1112 associated with print head 1009. Print head 1009 includes a plurality of microfluidic printing channels 1115, each stemming from respective fluid inlets 1112. The plurality of microfluidic printing channels 1115 in turn merge within print head 1009 into single dispensing channel 1015, leading to dispensing orifice 1018. Also illustrated at FIG. 11A are openings 1116 capable to receive mounting pins, for assisting in mounting of the back plate 1012, adaptor 1005, and print head 1009 to a printing system of the present disclosure (e.g., printing system 100 at FIG. 1A).

Although not explicitly illustrated at FIG. 11A, in embodiments print head 1009 may comprise an image, for example a machine-readable image. Similar to that discussed above, in embodiments, the image comprises a code (e.g., two dimensional bar code such as a QR code, microQR code, and the like) which can be scanned by a camera associated with printing systems (e.g., printing system 100) of the present disclosure. Information stored in the code can then be extracted, for example via a computing device associated with a control system (e.g., control system 102) and correspondingly used, in similar fashion as that discussed above.

Turning to FIG. 11B, depicted is a transparent side view of print head 1009 coupled to adaptor 1005 and back plate 1012. In other words, FIG. 11B represents the illustration of FIG. 11A rotated 90° about vertical axis 1130 depicted at FIG. 11A. Viewable from this transparent side view are syringe inlets 1011, microfluidic adaptor channels 1105, valves 1110, microfluidic printing channels 1115, dispensing channel 1015, and dispensing orifice 1018. Also viewable are openings 1116 included as part of back plate 1012, capable to receive mounting pins (not shown) as discussed above.

Adaptors of the present disclosure may be capable to fluidically couple with a variety of different print heads.

Thus, while particular print heads and configurations are shown, for example in FIGS. 9A-9B and FIGS. 11A-11B, it may be understood that such examples are illustrative and are not meant to be limiting. Thus, the adaptors of the present disclosure impart a modular aspect to the printing systems discussed herein, such that print heads can readily be exchanged depending on a desired use case.

For example, in some embodiments, print heads that can be used with the printing systems of the present disclosure can include one or more (e.g., 1, 2, 3, 4, 5, 6) fluidic focusing chambers comprised of a conical frustum shape configured to focus fluid toward the print head dispensing channel. For reference and without limitation, FIG. 9A depicts two such fluidic focusing chambers (first fluidic focusing chamber 926 and second fluidic focusing chamber 927), and FIG. 11A also depicts two such fluidic focusing chambers (first fluidic focusing chamber 1126 and second fluidic focusing chamber 1127). Relevant examples of print heads that include such fluidic focusing chambers are described in WO 2020/056517 and WO 2021/081672, the contents of each of which are incorporated by reference herein in their entirety.

Quality Control Systems:

Quality assurance for 3D bioprinting of fibers via printing systems, such as that disclosed herein, is vital to reproducible biofiber fabrication, function, and regulatory approval for any translational application. Accordingly, printing systems of the present disclosure (e.g., printing system 100) can incorporate one or more of the below-discussed quality control systems. In embodiments, a quality control system comprises one or more cameras. In embodiments, the one or more cameras are the same or different than a camera that is used to scan a code (e.g., QR code, microQR code, etc.) as described above, for inferring one or more of dimensions of the print head, number of fluid inlets fluidically coupled in turn to microfluidic channels, spacing of said fluid inlets in relation to one another, and the like.

In an exemplary embodiment, the camera directed to the back of the print head for purposes of scanning the code for coordination of the syringe pump assembly can also be used to image the interior of the print head itself, for purposes of detecting a clog or other aberration in material flow through the print head.

In embodiments, a print head used in conjunction with printing systems of the present disclosure comprises a transparent dispensing channel (e.g., dispensing channel 114). In such embodiments, a camera system comprises a first camera positioned at a first angle with respect to the transparent dispensing channel, and a second camera positioned at a second, different angle with respect to the transparent dispensing channel. In embodiments, the two cameras are oriented at about a 90° angle with respect to one another. The first camera and the second camera form part of a machine-learning based system capable of identifying one or more deviations in the material flow from user-established material flow parameters. For example, such a system may be capable of monitoring fiber diameter, concentricity and/or speed, various fiber properties, presence or absence of clogs, bubbles, and the like, and controlling one or more parameters (e.g., valve opening/closing, material flow rate, and the like) based on said monitoring. For instance, certain embodiments may enable contactless sensing of fiber formation, and provide automated analyses in order to derive quantitative measures of printed fiber properties including, for example, quality control/quality assurance parameters. In some embodiments, such quantitative measures may include real-time high-level quantitation of biological material (e.g., cells) throughout a fiber during printing.

In some embodiments, different machine-learning tools may be employed with the radial pump assembly. For example, convolutional neural networks (CNN) may be used for object detection. As another example, semantic segmentation may be used to monitor and analyze different properties of the print head and resulting fiber during printing.

In embodiments, outputs of the various machine-learning tools can be fed back in real-time to the 3D bioprinting platform in order to adjust the pressure and/or displacement and subsequent flow of materials within the microfluidic channels of the print head to correct for diameter and/or misconcentricity, thus enabling consistent production of quality fibers and minimizing the loss of expensive biomaterial and cell inputs in bioprinted fibers.

Certain embodiments may include a light emitting diode (LED) or LED array for each of the cameras, to illuminate transparent features of the microfluidic print head and the fibers within it. In embodiments, the cameras may be positioned in various ways in the printing system to optimally capture views of the nozzle, edges of an inner nozzle (the inner diameter, within which the fibers may be formed), as well as the fiber being produced (e.g., in the case of a concentric fiber, the shell and the core), may be visible in the camera views. Thus, according to some embodiments, the application of cameras in the printing system may allow for the ability to focus on various angles of the nozzle of the print head, and to monitor the nozzle, as well as various fiber characteristics including but not limited to, for example, distribution and/or consistency of concentration, cell count, and/or architecture of the fibers. Additional features of the cameras and machine-learning/artificial intelligence are described in U.S. Patent Application No. 62/238,028 and International Patent Application No. PCT/US2022/41759, the disclosures of which are hereby incorporated by reference in their entirety.

In embodiments, one or more additional or alternative cameras can be included as part of printing systems of the present disclosure. In one such embodiment, a camera(s) can be aimed at the receiving surface (e.g., receiving surface 121) so as to be capable to image the bioprinted fiber structure as it is printed. In this way, said camera(s) may be used to monitor for one or more properties of fibers dispensed from a print head (e.g., printhead 110). Such properties can include but are not limited to presence and/or absence of leading and/or trailing fibers and shape fidelity of printed fibers and/or 3D structures formed from said printed fibers.

In embodiments, the ring-shaped light module may comprise a part of a quality control system, in that the ring-shaped light module may serve to ensure uniformity of crosslinking of fibers comprised of a photo crosslinkable material as they are printed.

It is also herein recognized that use of pneumatic valves can be advantageous in the context of the present disclosure in terms of reducing or avoiding inaccuracies or distortions of desired 3D structures. For example, reliance on one or more pneumatic valves in conjunction with printing systems of the present disclosure can reduce or avoid inaccurate commencement and/or cessation of the printing process, which may otherwise result in the formation of leading and/or trailing fibers that may distort the dimensions of printed fibers and 3D structures. Specifically, it is herein recognized that reliance on pneumatic valve(s) can help to establish abrupt fiber initiation and termination. Accordingly, in embodiments, one or more pneumatic valve(s) may be used in conjunction with printing systems of the present disclosure to ensure that a fiber dispensed by the print head is terminated with a clean end that does not include a trailing fiber and/or to ensure that a fiber structure produced by the print head has a clean starting end that does not include a leading fiber.

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

What is claimed is:

1. A pump assembly configured for a bioprint system comprising a plurality of pumps positioned in a radial array on a mounting bracket, wherein one or more of said plurality of pumps is a syringe pump comprising a housing comprising a syringe retainer and a plunger driver, at least one syringe having a syringe barrel retained in place by a syringe retainer in at least one of said syringe pumps, wherein said syringe further comprises a syringe plunger slidably engaged with the syringe barrel and a plunger flange received by a plunger cap adjacent the plunger driver, the plunger cap configured to receive plunger flanges of differing dimensions, wherein the plunger cap comprises a concave surface for receiving the plunger driver.

2. The pump assembly according to claim 1, wherein said plurality of pumps are positioned in a radial array between 10 and 170 degrees relative to each other.

3. The pump assembly according to claim 1 or 2, wherein one or more of said plurality of pumps are removably attached to syringe bays on said mounting bracket; optionally wherein said housing magnetically attaches to said syringe bay.

4. The pump assembly according to claim 1, wherein said housing is wedge-shaped.

5. The pump assembly according to claim 1, wherein said plurality of pumps further comprises at least one peristaltic pump, constant-flow dual piston pump, gear pump, or combinations thereof.

6. The pump assembly according to claim 1, wherein more than one, most or all of said plurality of pumps are syringe pumps.

7. The pump assembly according to claim 1 wherein the concave surface comprises an inverted cone shape.

8. The pump assembly according to claim 1, wherein said syringe pump comprising said syringe further comprises one or more removable plunger clips for securing the plunger flange within the plunger cap.

9. The pump assembly according to claim 8, wherein said one or more plunger clips comprise a recess of different dimensions for fittingly engaging different syringe plunger diameters.

10. The pump assembly according to claim 8 or 9, wherein the plunger clip magnetically attaches to the plunger driver.

11. The pump assembly according to claim 1, wherein said syringe retainer comprises one of a plurality of removable syringe barrel supports, each of said syringe barrel supports comprising a recess of different dimensions for fittingly engaging different syringe barrel diameters.

12. The pump assembly of claim 11, wherein each of said syringe barrel supports further comprise a slot configured to receive and secure a syringe barrel flange.

13. The pump assembly according to claim 1, wherein a syringe barrel centerline is maintained as constant between syringes of different dimensions.

14. The pump assembly according to claim 1, wherein said at least one syringe is a disposable syringe; optionally wherein said disposable syringe differs in size between 0.2 ml and 50 ml.

15. A multi-channel microfluidic bioprinting system comprising:

- a print head comprising a plurality of fluid inlets and a plurality of microfluidic printing channels corresponding to each fluid inlet, wherein the plurality of microfluidic channels merge into a single dispensing channel leading to a dispensing orifice;
- a pump assembly according to claim 1,
- an adaptor comprising a plurality of pump inlets and corresponding microfluidic adaptor channels for fluidly connecting one or more of said pumps to said print head;
- a receiving surface for receiving a first layer of materials dispensed from the orifice;
- a positioning unit for positioning the receiving surface in three dimensional space with respect to the dispensing orifice, the positioning unit operably coupled to the receiving surface; and
- a programmable control processor for controlling the positioning unit and for controlling each syringe pump.

16. The multi-channel microfluidic bioprinting system according to claim 15 wherein said pump assembly comprises a plurality of syringes retained in a plurality of said syringe pumps.

17. The multi-channel microfluidic bioprinting system according to claim 16, wherein a tip of each of said syringes insert into corresponding fluid inlets in said adaptor.

18. The multi-channel microfluidic bioprinting system according to claim 16, wherein a tip of each of said syringes further comprise an elbow connector for inserting into corresponding fluid inlets in said adaptor.

19. The multi-channel microfluidic bioprinting system according to claim 16, wherein the tip of a central syringe inserts directly into a fluid inlet of the print head, thereby bypassing said adaptor.

20. The multi-channel microfluidic bioprinting system according to claim 15, wherein the microfluidic adaptor channels and/or the microfluidic printing channels further comprise valves, optionally wherein said valves are one-way check valves.

21. The multi-channel microfluidic bioprinting system according to claim 15, further comprising a fluid removal component that is configured to remove an excess fluid that is dispensed from the print head.

22. The multi-channel microfluidic bioprinting system of claim 15, further comprising a camera configured to capture a machine-readable image included as part of the print head.

23. The multi-channel microfluidic bioprinting system of claim 22, wherein the machine-readable image is a quick response (QR) code.

24. The multi-channel microfluidic bioprinting system of claim 22 or 23, wherein the programmable control processor provides a visual alert to a user of the system upon acquisition of the machine-readable image, the visual alert comprising an indication to the user of where to attach one or more of the syringe pumps to the mounting bracket, and/or in which syringe pumps to insert a syringe.

25. The multi-channel microfluidic bioprinting system of claim 24, wherein the visual alert is based on one or more lights on the mounting bracket and/or syringe pumps.

26. The multi-channel microfluidic bioprinting system of claim 15, further comprising a ring-shaped light module configured to surround the dispensing channel.

27. The multi-channel microfluidic bioprinting system of claim 15, further comprising an enclosure system.

* * * * *